United States Patent
Smith et al.

(10) Patent No.: US 10,568,973 B2
(45) Date of Patent: Feb. 25, 2020

(54) OPTIMIZED RPE65 PROMOTER AND CODING SEQUENCES

(71) Applicant: UCL BUSINESS LTD, London (GB)

(72) Inventors: Alexander Smith, London (GB); Robin Ali, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 15/549,549

(22) PCT Filed: Feb. 8, 2016

(86) PCT No.: PCT/GB2016/050289
§ 371 (c)(1),
(2) Date: Aug. 8, 2017

(87) PCT Pub. No.: WO2016/128722
PCT Pub. Date: Aug. 18, 2016

(65) Prior Publication Data
US 2018/0021458 A1   Jan. 25, 2018

(30) Foreign Application Priority Data
Feb. 9, 2015   (GB) .................................. 1502137.1

(51) Int. Cl.
*A61K 48/00* (2006.01)
*C12N 15/85* (2006.01)
*C12N 15/861* (2006.01)

(52) U.S. Cl.
CPC ...... *A61K 48/0058* (2013.01); *C12N 15/8509* (2013.01); *C12Y 301/01064* (2013.01); *C12N 15/861* (2013.01); *C12N 2015/8518* (2013.01)

(58) Field of Classification Search
CPC .............................. A61K 18/0058; C12N 15/85
See application file for complete search history.

(56) References Cited

U.S. PATENT DOCUMENTS

2007/0258950 A1   11/2007   Auricchio et al.

FOREIGN PATENT DOCUMENTS

| WO | 2009/105690 A2 | 8/2009 |
| WO | 2013/164793 A2 | 11/2013 |
| WO | 2013/173129 A2 | 11/2013 |

OTHER PUBLICATIONS

Bainbridge, J. et al., "Effect of Gene Therapy on Visual Function in Leber's Congenital Amaurosis"; NEJM (2008); vol. 358:21; pp. 2231-2239.
Cideciyan, A. V. et al., "Human Gene Therapy for RPE65 Isomerase Deficiency Activates the Retinoid Cycle of Vision but with Slow Rod Kinetics"; PNAS USA (2008); vol. 105:39; pp. 15112-15117.
Cideciyan, A. V. et al., "Vision 1 Year After Gene Therapy for Leber's Congenital Amaurosis"; N. Engl. J. Med. (2009); vol. 361:7; pp. 725-727.
Hauswirth, W. et al., "Treatment of Leber Congenital Amaurosis due to RPE65 Mutations by Ocular Subretinal Injection of Adeno-Associated Virus Gene Vector: Short-Term Results of a Phase 1 Trial"; Hum. Gene Ther. (2008); vol. 19; pp. 979-990.
Le Meur, G. et al., "Restoration of Vision in RPE65-Deficient Briard dogs using an AAV Serotype 4 Vector that Specifically Targets the Retinal Pigmented Epithelium"; Gene Therapy (2007); vol. 14: pp. 292-303.
Maguire, A. M. et al., "Age-Dependent Effects of Rpe65 Gene Therapy for Leber's Congenital Amaurosis; A Phase 1 Dose-Escalation Trial"; The Lancet (2009); vol. 374; pp. 1597-1605.
Smith, A. J. et al., "Prospects for Retinal Gene Replacement Therapy"; Trends in Genetics (2009); vol. 25:4; pp. 156-165.
Smith, A.J. et al., "Gene Supplementation Therapy for Recessive forms of Inherited Retinal Dystrophies"; Gene Therapy (2012); vol. 19; pp. 154-161.
Database Geneseq [Online]; "AMD Treatment-Related Promoter Sequence, Seq. ID No. 30"; retrived from EBI accession No. GSN: BAY70761 (2014); 1 pg.

*Primary Examiner* — Antonio Galisteo Gonzalez
(74) *Attorney, Agent, or Firm* — Fox Rothschild LLP

(57) ABSTRACT

The present invention relates to the prevention and/or treatment of retinal dystrophyin a patient, including Leber congenital amaurosis (LCA).

21 Claims, 3 Drawing Sheets

Specification includes a Sequence Listing.

1: AAV2/8.RPE65.GFP
2: AAV2/8.NA.GFP
3: AAV2/8.BGL.GFP
4: uninjected control

1: AAV2/8.NA.GFP
2: AAV2/8.NA.GFP (1:20 dilution)
3: AAV2/8.BGL.GFP
4: AAV2/8.RPE65.GFP

A

B

B-y axis label- protein expression relative to H2B loading control.

SEQUENCE LISTING

<160> NUMBER OF SEQ ID NOS: 14

<210> SEQ ID NO 1
<211> LENGTH: 1614
<212> TYPE: DNA
<213> ORGANISM: Homo sapiens

<400> SEQUENCE: 1

| | | | | | | |
|---|---|---|---|---|---|---|
| tattgtgcaa | ataagtgctc | actccaaatt | agtggtatat | ttattgaagt | ttaatattgt | 60 |
| gtttgtgata | cagaagtatt | tgctttaatt | ctaaataaaa | attttatgct | tttattgctg | 120 |
| gtttaagaag | atttggatta | tccttgtact | ttgaggagaa | gtttcttatt | tgaaatattt | 180 |
| tggaaacagg | tcttttaatg | tggaaagata | gatattaatc | tcctcttcta | ttactctcca | 240 |
| agatccaaca | aaagtgatta | tacccccaa | aatatgatgg | tagtatctta | tactaccatc | 300 |
| attttatagg | catagggctc | ttagctgcaa | ataatgaac | taactctaat | aaagcagaac | 360 |
| gcaaatattg | taaatattag | agagctaaca | atctctggga | tggctaaagg | atggagcttg | 420 |
| gaggctaccc | agccagtaac | aatattccgg | gctccactgt | tgaatggaga | cactacaact | 480 |
| gccttggatg | ggcagagata | ttatggatgc | taagccccag | gtgctaccat | taggacttct | 540 |
| accactgtcc | ctaacgggtg | gagcccatca | catgcctatg | ccctcactgt | aaggaaatga | 600 |
| agctactgtt | gtatatcttg | ggaagcactt | ggattaattg | ttatacagtt | tgttgaaga | 660 |
| agacccctag | ggtaagtagc | cataactgca | cactaaattt | aaaattgtta | atgagtttct | 720 |
| caaaaaaat | gttaaggttg | ttagctggta | tagtatatat | cttgcctgtt | ttccaaggac | 780 |
| ttctttgggc | agtaccttgt | ctgtgctggc | aagcaactga | gacttaatga | aagagtattg | 840 |
| gagatatgaa | tgaattgatg | ctgtatactc | tcagagtgcc | aaacatatac | caatggacaa | 900 |
| gaaggtgagg | cagagagcag | acaggcatta | gtgacaagca | aagatatgca | gaatttcatt | 960 |
| ctcagcaaat | caaagtcct | caacctggtt | ggaagaatat | tggcactgaa | tggtatcaat | 1020 |
| aaggttgcta | gagagggtta | gaggtgcaca | atgtgcttcc | ataacatttt | atacttctcc | 1080 |
| aatcttagca | ctaatcaaac | atggttgaat | actttgttta | ctataactct | tacagagtta | 1140 |
| taagatctgt | gaagacaggg | acagggacaa | tacccatctc | tgtctggttc | ataggtggta | 1200 |
| tgtaatagat | attttaaaa | ataagtgagt | taatgaatga | gggtgagaat | gaaggcacag | 1260 |
| aggtattagg | gggaggtggg | ccccagagaa | tggtgccaag | gtccagtggg | gtgactggga | 1320 |
| tcagctcagg | cctgacgctg | gccactccca | cctagctcct | ttctttctaa | tctgttctca | 1380 |
| ttctccttgg | gaaggattga | ggtctctgga | aaacagccaa | acaactgtta | tgggaacagc | 1440 |
| aagcccaaat | aaagccaagc | atcaggggga | tctgagagct | gaaagcaact | tctgttcccc | 1500 |
| ctccctcagc | tgaaggggtg | gggaagggct | cccaaagcca | taactccttt | taagggattt | 1560 |
| agaaggcata | aaaaggcccc | tggctgagaa | cttccttctt | cattctgcag | ttgg | 1614 |

<210> SEQ ID NO 2
<211> LENGTH: 761
<212> TYPE: DNA
<213> ORGANISM: Artificial Sequence
<220> FEATURE:
<223> OTHER INFORMATION: Optimised human RPE65 promoter fragment

<400> SEQUENCE: 2

```
agatcttcga aatactctca gagtgccaaa catataccaa tggacaagaa ggtgaggcag      60
agagcagaca ggcattagtg acaagcaaag atatgcagaa tttcattctc agcaaatcaa     120
aagtcctcaa cctggttgga agaatattgg cactgaatgg tatcaataag gttgctagag     180
agggttagag gtgcacaatg tgcttccata acattttata cttctccaat cttagcacta     240
atcaaacatg gttgaatact ttgtttacta taactcttac agagttataa gatctgtgaa     300
gacagggaca gggacaatac ccatctctgt ctggttcata ggtggtatgt aatagatatt     360
tttaaaaata agtgagttaa tgaatgaggg tgagaatgaa ggcacagagg tattaggggg     420
aggtgggccc cagagaatgg tgccaaggtc cagtggggtg actgggatca gctcaggcct     480
gacgctggcc actcccacct agctcctttc tttctaatct gttctcattc ccttgggaa      540 ggattgaggt ctctggaaaa cagccaaaca actgttatgg gaacagcaag cccaaataaa     600
gccaagcatc aggggggatct gagagctgaa agcaacttct gttccccctc cctcagctga   660
aggggtgggg aagggctccc aaagccataa ctccttttaa gggatttaga aggcataaaa    720
aggcccctgg ctgagaactt ccttcttcat tctgcagttg g                        761
```

<210> SEQ ID NO 3
<211> LENGTH: 1602
<212> TYPE: DNA
<213> ORGANISM: Homo sapiens

<400> SEQUENCE: 3

```
atgtctatcc aggttgagca tcctgctggt ggttacaaga aactgtttga aactgtggag      60
gaactgtcct cgccgctcac agctcatgta acaggcagga tcccctctg gctcaccggc     120 agtctccttc gatgtgggcc aggactcttt gaagttggat ctgagccatt ttaccacctg     180
tttgatgggc aagccctcct gcacaagttt gactttaaag aaggacatgt cacataccac     240
agaaggttca tccgcactga tgcttacgta cgggcaatga ctgagaaaag gatcgtcata     300
acagaatttg gcacctgtgc tttcccagat ccctgcaaga atatattttc caggtttttt     360
tcttactttc gaggagtaga ggttactgac aatgcccttg ttaatgtcta cccagtgggg     420
gaagattact acgcttgcac agagaccaac tttattacaa agattaatcc agagaccttg     480
gagacaatta gcaggttga tctttgcaac tatgtctctg tcaatggggc cactgctcac     540
ccccacattg aaaatgatgg aaccgtttac aatattggta attgctttgg aaaaaatttt     600
tcaattgcct acaacattgt aaagatccca ccactgcaag cagacaagga agatccaata     660
agcaagtcag agatcgttgt acaattcccc tgcagtgacc gattcaagcc atcttacgtt     720 catagtttg gtctgactcc caactatatc gtttttgtgg agacaccagt caaaattaac     780
ctgttcaagt tccttttcttc atggagtctt tggggagcca actacatgga ttgttttgag     840
tccaatgaaa ccatggggt ttggcttcat attgctgaca aaaaaaggaa aaagtaccctc    900 aataataaat acagaacttc tccttttcaac ctcttccatc acatcaacac ctatgaagac     960
aatgggtttc tgattgtgga tctctgctgc tggaaaggat ttgagtttgt ttataattac    1020
ttatatttag ccaatttacg tgagaactgg gaagaggtga aaaaaaaatgc cagaaaggct   1080
```

```
ccccaaccctg aagttaggag atatgtactt cctttgaata ttgacaaggc tgacacaggc   1140
aagaatttag tcacgctccc caatacaact gccactgcaa ttctgtgcag tgacgagact   1200
atctggctgg agcctgaagt tctcttttca gggcctcgtc aagcatttga gtttcctcaa   1260
atcaattacc agaagtattg tgggaaacct tacacatatg cgtatggact tggcttgaat   1320
cactttgttc cagataggct ctgtaagctg aatgtcaaaa ctaaagaaac ttgggtttgg   1380
caagagcctg attcataccc atcagaaccc atctttgttt ctcacccaga tgccttggaa   1440
gaagatgatg gtgtagttct gagtgtggtg gtgagcccag gagcaggaca aaagcctgct   1500
tatctcctga ttctgaatgc caaggactta agtgaagttg cccgggctga agtggagatt   1560
aacatccctg tcacctttca tggactgttc aaaaaatctt ga                     1602
```

<210> SEQ ID NO 4
<211> LENGTH: 1607
<212> TYPE: DNA
<213> ORGANISM: Artificial Sequence
<220> FEATURE:
<223> OTHER INFORMATION: Optimised human RPE65 coding sequence

<400> SEQUENCE: 4

```
ccaccatgag tatccaggtg aacatcccg caggggggta taagaaactg tttgagaccg    60
tcgaagaact gagcagccct ctgaccgcac atgtcaccgg aagaatcccc ctgtggctga   120
caggatcact gctgagatgc ggaccaggac tgttcgaagt gggaagcgaa cctttctacc   180
acctgtttga cggacaggcc ctgctgcata gttcgactt caaggagggg cacgtgactt    240
accatcggcg gttcatccga accgacgcct atgtccgggc tatgacagag aagagaatcg   300
tgattactga gttcggcacc tgcgcctttc cagatccctg taagaacatt ttctccaggt   360
tcttttctta ctttcgcggc gtcgaggtga cagacaacgc actggtcaac gtgtaccctg   420 tggggggagga ttactatgcc tgcactgaaa ccaacttcat caccaagatt aatccagaga   480
cactggaaac tatcaaacag gtggacctgt gcaactacgt cagtgtgaat ggcgccaccg   540 ctcacccca tccgagaac gatgggacag tctacaacat tggcaattgc ttcgggaaga   600
actttagcat cgcctacaac atcgtgaaga tccccctct gcaggctgac aaggaggatc   660
ctatctctaa aagtgaaatt gtggtccagt tcccttgttc tgaccggttt aagccaagtt   720
acgtccactc attcggcctg acaccaaact atatcgtctt tgtggagact cccgtgaaga   780
ttaatctgtt caaatttctg agctcctggt ctctgtgggg ggctaactac atggactgct   840
tcgagagtaa tgaaacaatg ggagtgtggc tgcacatcgc agataagaaa cgaaagaaat   900
acctgaacaa taagtaccgg actagccct tcaacctgtt tcaccatatc aacacctatg   960
aggacaatgg atttctgatt gtcgatctgt gctgttggaa gggcttcgag ttcgtgtaca   1020
actatctgta cctggcaaac ctgcgcgaaa ttggggaga agtgaagaaa aatgctcgaa   1080
aagcacctca gccagaagtc aggcgctacg tgctgcccact gaacatcgac aaggctgata   1140
caggcaaaaa cctggtgact ctgcccaata ccacagcaac tgccatcctg tgctccgacg   1200
agaccatttg gctggagccc gaagtgctgt tctctggacc tcgccaggcc ttcgaatttc   1260
cacagattaa ttaccagaag tactgcggca accctatac ctacgcttat ggactgggcc   1320
tgaaccactt cgtgcctgat agactgtgca agctgaatgt caagaccaaa gagacatggg   1380
tgtggcagga acctgactca taccccagcg agcctatctt tgtgagccat ccagatgccc   1440
tggaggaaga cgatgcgtg gtcctgagcg tggtcgtgtc cccaggagca ggacagaagc   1500
cagcctatct gctgattctg aacgctaaag atctgtccga agtggcaaga gcagaggtgg   1560
```

```
agatcaatat cccagtcaca tttcacgggc tgttcaaaaa gtcctaa            1607
```

<210> SEQ ID NO 5
<211> LENGTH: 3000
<212> TYPE: DNA
<213> ORGANISM: Homo sapiens

<400> SEQUENCE: 5

```
atggggccgg ccccgctgcc gctgctgctg ggcctcttcc tccccgcgct ctggcgtaga     60
gctatcactg aggcaaggga agaagccaag ccttacccgc tattcccggg accttttcca    120
gggagcctgc aaactgacca cacccgctg ttatcccttc ctcacgccag tgggtaccag    180
cctgccttga tgttttcacc aacccagcct ggaagaccac atacaggaaa cgtagccatt    240
ccccaggtga cctctgtcga atcaaagccc ctaccgcctc ttgccttcaa acacacagtt    300
ggacacataa tactttctga acataaaggt gtcaaattta attgctcaat cagtgtacct    360
aatatatacc aggacaccac aatttcttgg tggaaagatg ggaaggaatt gcttggggca    420
catcatgcaa ttacacagtt ttatccagat gatgaagtta cagcaataat cgcttccttc    480
agcataacca gtgtgcagcg ttcagacaat gggtcgtata tctgtaagat gaaaataaac    540
aatgaagaga tcgtgtctga tcccatctac atcgaagtac aaggacttcc tcactttact    600
aagcagcctg agagcatgaa tgtcaccaga aacacagcct tcaacctcac ctgtcaggct    660
gtgggcccgc tgagcccgt caacattttc tgggttcaaa acagtagccg tgttaacgaa    720
cagcctgaaa atcccctc cgtgctaact gttccaggcc tgacggagat ggcggtcttc    780
agttgtgagg cccacaatga caaagggctg accgtgtcca agggagtgca gatcaacatc    840
aaagcaattc cctccccacc aactgaagtc agcatccgta acagcactgc acacagcatt    900
ctgatctcct gggttcctgg ttttgatgga tactccccgt tcaggaattg cagcattcag    960
gtcaaggaag ctgatccgct gagtaatggc tcagtcatga ttttaacac ctctgccta   1020
ccacatctgt accaaatcaa gcagctgcaa gccctggcta attacagcat tggtgttcc   1080
tgcatgaatg aaataggctg tctgcagtg agcccttgga ttctagccag cacgactgaa   1140
ggagccccat cagtagcacc tttaaatgtc actgtgtttc tgaatgaatc tagtgataat   1200
gtggacatca gatggatgaa gcctccgact aagcagcagg atggagaact ggtgggctac   1260
cggatatccc acgtgtggca gagtgcaggg atttccaaag agctcttgga ggaagttggc   1320
cagaatggca gccgagctcg gatctctgtt caagtccaca atgctacgtg cacagtgagg   1380
attgcagccg tcaccagagg gggagttggg cccttcagtg atccagtgaa atattatc   1440
cctgcacacg gttgggtaga ttatgccccc tcttcaactc cggcgcctgg caacgcagat   1500
cctgtgctca tcatctttgg ctgcttttgt ggatttattt tgattgggtt gattttatac   1560
atctccttgg ccatcagaaa aagagtccag gagacaaagt ttgggaatgc attcacagag   1620
gaggattctg aattagtggt gaattatata gcaaagaaat ccttctgtcg gcgagccatt   1680
gaacttacct tacatagctt gggagtcagt gaggaactac aaaataaact agaagatgtt   1740
gtgattgaca ggaatcttct aattcttgga aaaattctgg gtgaaggaga gtttgggtct   1800
gtaatggaag aaatcttaa gcaggaagat gggacctctc tgaaagtggc agtgaagacc   1860
atgaagttgg acaactcttc acagcgggag atcgaggagt ttctcagtga ggcagcgtgc   1920
atgaaagact tcagccaccc aaatgtcatt cgacttctag gtgtgtgtat agaaatgagc   1980
tctcaaggca tcccaaagcc catggtaatt ttacccttca tgaaatacgg ggacctgcat   2040
```

| | |
|---|---|
| acttacttac tttattcccg attggagaca ggaccaaagc atattcctct gcagacacta | 2100 |
| ttgaagttca tggtggatat tgccctggga atggagtatc tgagcaacag gaattttctt | 2160 |
| catcgagatt tagctgctcg aaactgcatg ttgcgagatg acatgactgt ctgtgttgcg | 2220 |
| gacttcggcc tctctaagaa gatttacagt ggcgattatt accgccaagg ccgcattgct | 2280 |
| aagatgcctg ttaaatggat cgccatagaa agtcttgcag accgagtcta cacaagtaaa | 2340 |
| agtgatgtgt gggcatttgg cgtgaccatg tgggaaatag ctacgcgggg aatgactccc | 2400 |
| tatcctgggg tccagaacca tgagatgtat gactatcttc tccatggcca caggttgaag | 2460 |
| cagcccgaag actgcctgga tgaactgtat gaaataatgt actcttgctg gagaaccgat | 2520 |
| cccttagacc gccccacctt ttcagtattg aggctgcagc tagaaaaact cttagaaagt | 2580 |
| ttgcctgacg ttcggaacca gcagacgtt atttacgtca atacacagtt gctggagagc | 2640 |
| tctgagggcc tggcccaggg ctccacccttt gctccactgg acttgaacat cgaccctgac | 2700 |
| tctataattg cctcctgcac tccccgcgct gccatcagtg tggtcacagc agaagttcat | 2760 |
| gacagcaaac ctcatgaagg acggtacatc ctgaatgggg gcagtgagga atgggaagat | 2820 |
| ctgacttctg cccctctgc tgcagtcaca gctgaaaaga acagtgtttt accgggggag | 2880 |
| agacttgtta ggaatggggt ctcctggtcc cattcgagca tgctgcccctt gggaagctca | 2940 |
| ttgcccgatg aacttttgtt tgctgacgac tcctcagaag gctcagaagt cctgatgtga | 3000 |

<210> SEQ ID NO 6
<211> LENGTH: 693
<212> TYPE: DNA
<213> ORGANISM: Homo sapiens

<400> SEQUENCE: 6

| | |
|---|---|
| atgaagaacc ccatgctgga ggtggtgtct ttactactgg agaagctgct cctcatctcc | 60 |
| aacttcacgc tctttagttc gggcgccgcg ggcgaagaca agggaggaa cagttttat | 120 |
| gaaaccagct ctttccaccg aggcgacgtg ctggaggtgc cccggaccca cctgacccac | 180 |
| tatggcatct acctaggaga caaccgtgtt gcccacatga tgcccgacat cctgttggcc | 240 |
| ctgacagacg acatggggcg cacgcagaag gtggtctcca acaagcgtct catcctgggc | 300 |
| gttattgtca aagtggccag catccgcgtg gacacagtgg aggacttcgc ctacggagct | 360 |
| aacatcctgg tcaatcacct ggacgagtcc ctccagaaaa aggcactgct caacgaggag | 420 |
| gtggcgcgga gggctgaaaa gctgctgggc tttacccccct acagcctgct gtggaacaac | 480 |
| tgcgagcact cgtgacccta ctgcagatat ggcaccccga tcagtcccca gtccgacaag | 540 |
| ttttgtgaga ctgtgaagat aattattcgt gatcagagaa gtgttcttgc ttcagcagtc | 600 |
| ttgggattgg cgtctatagt ctgtacgggc ttggtatcat acactaccct tcctgcaatt | 660 |
| tttattccat tcttcctatg gatggctggc taa | 693 |

<210> SEQ ID NO 7
<211> LENGTH: 1590
<212> TYPE: DNA
<213> ORGANISM: Homo sapiens

<400> SEQUENCE: 7

| | |
|---|---|
| atgctcctgg ctgttttgta ctgcctgctg tggagtttcc agacctccgc tggccatttc | 60 |
| cctagagcct gtgtctcctc taagaacctg atggagaagg aatgctgtcc accgtggagc | 120 |
| ggggacagga gtccctgtgg ccagcttca ggcagaggtt cctgtcagaa tatccttctg | 180 |
| tccaatgcac cacttgggcc tcaatttccc ttcacagggg tggatgaccg ggagtcgtgg | 240 |

```
ccttccgtct tttataatag gacctgccag tgctctggca acttcatggg attcaactgt     300
ggaaactgca agtttggctt ttggggacca aactgcacag agagacgact cttggtgaga     360
agaaacatct tcgatttgag tgccccagag aaggacaaat tttttgccta cctcacttta     420
gcaaagcata ccatcagctc agactatgtc atccccatag gacctatgg ccaaatgaaa      480 aatggatcaa cacccatgtt taacgacatc aatatttatg acctctttgt ctggatgcat     540
tattatgtgt caatggatgc actgcttggg ggatctgaaa tctggagaga cattgatttt     600
gcccatgaag caccagcttt tctgccttgg catagactct tcttgttgcg gtgggaacaa     660
gaaatccaga agctgacagg agatgaaaac ttcactattc catattggga ctggcgggat     720
gcagaaaagt gtgacatttg cacagatgag tacatgggag gtcagcaccc cacaaatcct     780
aacttactca gcccagcatc attcttctcc tcttggcaga ttgtctgtag ccgattggag     840
gagtacaaca gccatcagtc tttatgcaat ggaacgcccg agggaccttt acggcgtaat     900
cctggaaacc atgacaaatc cagaaccccca aggctcccct cttcagctga tgtagaattt     960
tgcctgagtt tgacccaata tgaatctggt tccatggata aagctgccaa tttcagcttt    1020
agaaatacac tggaaggatt tgctagtcca cttactggga tagcggatgc ctctcaaagc    1080
agcatgcaca atgccttgca catctatatg aatggaacaa tgtcccaggt acagggatct    1140
gccaacgatc ctatcttcct tcttcaccat gcatttgttg acagtatttt tgagcagtgg    1200
ctccgaaggc accgtcctct tcaagaagtt tatccagaag ccaatgcacc cattggacat    1260
aaccgggaat cctacatggt tccttttata ccactgtaca gaaatggtga tttctttatt    1320
tcatccaaag atctgggcta tgactatagc tatctacaag attcagaccc agactctttt    1380
caagactaca ttaagtccta tttggaacaa gcgagtcgga tctggtcatg gctccttggg    1440
gcggcgatgg taggggccgt cctcactgcc ctgctggcag ggcttgtgag cttgctgtgt    1500
cgtcacaaga gaaagcagct tcctgaagaa aagcagccac tcctcatgga gaaagaggat    1560
taccacagct tgtatcagag ccatttataa                                     1590
```

<210> SEQ ID NO 8
<211> LENGTH: 1275
<212> TYPE: DNA
<213> ORGANISM: Homo sapiens

<400> SEQUENCE: 8

```
atgacccagg caggccggcg gggtcctggc acacccgagc cgcgtccgcg aacacagccc      60
atggcctccc cgcgcctagg gaccttctgc tgccccacgc gggacgcagc cacgcagctc     120
gtgctgagct ccagccgcg ggccttccac gcgctctgcc tgggcagcgg cgggctccgc      180
ttggcgctgg ccttctgca gctgctgccc ggccgccggc ccgcgggccc cgggtccccc     240
gcgacgtccc cgccggcctc ggtccgcatc ctgcgcgctg ccgctgcctg cgaccttctc     300
ggctgcctgg gtatggtgat ccggtccacc gtgtggttag gattcccaaa ttttgttgac     360
agcgtctcgg atatgaacca cacggaaatt tggcctgctg ctttctgcgt ggggagtgcg     420
atgtggatcc agctgttgta cagtgcctgc ttctggtggc tgttttgcta tgcagtggat     480
gcttatctgg tgatccggag atcggcagga ctgagcacca tcctgctgta tcacatcatg     540
gcgtggggcc tggccaccct gctctgtgtg agggagccg ccatgctcta ctacccttcc      600
gtgtccaggt gtgagcgggg cctggaccac gccatccccc actatgtcac catgtacctg     660
cccctgctgc tggttctcgt ggcgaacccc atcctgttcc aaaagacagt gactgcagtg     720
```

```
gcctctttac ttaaaggaag acaaggcatt tacacggaga acgagaggag gatgggagcc    780
gtgatcaaga tccgattttt caaaatcatg ctggttttaa ttatttgttg gttgtcgaat    840
atcatcaatg aaagccttt attctatctt gagatgcaaa cagatatcaa tggaggttct    900
ttgaaacctg tcagaactgc agccaagacc acatggttta ttatgggaat cctgaatcca    960
gcccagggat ttctcttgtc tttggccttc tacggctgga caggatgcag cctgggtttt   1020
cagtctccca ggaaggagat ccagtgggaa tcactgacca cctcggctgc tgagggggct   1080
cacccatccc cactgatgcc ccatgaaaac cctgcttccg ggaaggtgtc tcaagtgggt   1140
gggcagactt ctgacgaagc cctgagcatg ctgtctgaag gttctgatgc cagcacaatt   1200
gaaattcaca ctgcaagtga atcctgcaac aaaaatgagg gtgaccctgc tctcccaacc   1260
catggagacc tatga                                                    1275
```

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
aattaccaaa tattgtaaac ggttccatc                                       29

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
tgtttgaaac tgtggaggaa ctgtc                                           25

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
gaagcgcgat cacatggt                                                   18

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
ccatgccgag agtgatcc                                                   18

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gtggtacgac cagaggcata c                                               21

```
<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
aaggccaacc gtgaaaagat                                               20
```

OPTIMIZED RPE65 PROMOTER AND CODING SEQUENCES

FIELD OF THE INVENTION

The present invention relates to gene therapy for the treatment and/or prevention of retinal dystrophies, in particular disorders of the retinal pigment epithelium, such as Leber congenital amaurosis.

BACKGROUND OF THE INVENTION

Retinal dystrophies, including inherited retinal dystrophies (IRDs), form a large group of genetically and phenotypically heterogeneous diseases that are characterised by progressive loss of photoreceptor cells and concomitant loss of vision. IRDs affect approximately 1 in 3000 people in Europe and the United States. To date about 200 genes and a further 50 loci associated with retinal dystrophy have been identified. The majority of these disorders are caused by loss-of-function mutations acquired by recessive or X-linked inheritance.

Substantial variation exists with respect to the onset, rate of vision loss, and the primary cell type affected. The most severe forms of inherited retinal degeneration are the various types of Leber congenital amaurosis (LCA), in which there is severe visual impairment from birth and often complete loss of vision during the first two decades. Although the primary cell type most commonly affected in retinal degeneration is the photoreceptor cell, defects in other cell types such as the retinal pigment epithelium (RPE) can lead to reduced photoreceptor function and their subsequent loss.

An example of an inherited retinal dystrophy owing to a defect in the RPE is a form of LCA caused by defects in the RPE-predominant iron-dependent retinoid isomerohydrolase RPE65, which accounts for between 6 and 16% of LCA cases. Its absence results in the disruption of the visual cycle leading to absent rod function and, consequently, to photoreceptor degeneration.

Several clinical and pre-clinical gene-replacement therapy studies have shown that subretinal delivery of adenoviral AAV2 vectors is safe, and can result in increased visual function (Bainbridge et al. 2008, Maguire et al. 2008, 2009, Hauswirth et al. 2008, Cideciyan et al 2008, 2009) and activity in the visual cortex (Ashtari et al. 2011).

However, in a previous investigation into gene-therapy replacement of RPE65 in the RPE (Bainbridge et al. 2008), the authors reported that though there were improvements to retinal sensitivity and visual-guided mobility in one patient upon treatment, there were no significant improvements in visual acuity and peripheral field vision. Additionally, there were no significant improvements in all measured parameters in the other treated patients. Improvements in electroretinographic responses have yet to be reported in any study. It has also been observed that treating RPE65−/− dogs at 30 months with AAV2/4 vector-mediated therapy did not rescue vision or retinal function (Le Meur et al. 2007).

Therefore, there is a need for improvements in gene-replacement therapies for retinal dystrophies, especially inherited retinal dystrophies, in particular for disorders of the retinal pigment epithelium (RPE) such as Leber congenital amaurosis.

SUMMARY OF THE INVENTION

The present invention is based on the creation of an optimised promoter for expressing genes in the RPE. This optimised promoter is shown in SEQ ID NO: 2. The promoter comprises nucleotides 865 to 1614 of the human RPE65 promoter used in Bainbridge et al. (2008), which is shown in SEQ ID NO:1. The use of this promoter in a vector to drive expression of a control gene in the RPE was effective with an expression level approximately 20× higher than that with the original RPE65 promoter. The optimised RPE65 promoter was both more potent than the original RPE65 promoter and more stringent in driving expression in RPE cells in relation to photoreceptor cells.

In addition, the native coding sequence of RPE65, which is shown in SEQ ID NO: 3, has been optimised to give an optimised sequence which is shown in SEQ ID NO: 4. The optimised RPE65 sequence was tested alongside the original RPE65 sequence in vitro in (human) 293T cells to determine the effect on RPE65 protein production levels, after transfection of an AAV2/8 expression plasmid carrying the ubiquitous CMV promoter. In vitro protein production in 293T cells after optimisation of the RPE65 coding sequence showed a seven-fold increase in the amount of RPE65 protein produced from the vector carrying the optimised coding sequence compared to the wild type coding sequence.

The optimised promoter and optimised RPE65 sequence have also been combined in a vector to test their ability to rescue retinal function in vivo in RPE65-deficient mice. Efficacy of rescue was compared against the clinical grade vector previously used in Bainbridge et al (2008). Lower vector doses were administered to allow comparison of treatment efficacy under limiting circumstances. b-wave amplitude was used as a measure of rescue. Surprisingly, the b-wave amplitudes from the eyes treated with the optimised vector were as high as or higher than amplitudes from eyes injected with a 300-fold higher dose of the original vector. Optimisation of the promoter and/or the coding sequence according to the invention is therefore highly advantageous compared to using the native sequences.

Accordingly, the invention provides a retinal pigment epithelium (RPE)-specific promoter which comprises: (a) a sequence of contiguous nucleotides from SEQ ID NO:1 that confers RPE-specific expression on an operably linked polynucleotide sequence, or (b) a sequence having at least 90% sequence identity to said sequence of (a) and that retains RPE-specific promoter activity.

In another related aspect, the invention provides an expression construct comprising a promoter of the invention, operably linked to a sequence to be expressed in an RPE-specific manner.

In another related aspect, the invention provides a vector comprising a promoter of the invention or an expression cassette of the invention.

In another related aspect, the invention provides a host cell that contains a vector of the invention or produces a viral vector of the invention.

In another related aspect, the invention provides a pharmaceutical composition comprising a vector of the invention and a pharmaceutically acceptable carrier.

In another related aspect, the invention provides a vector of the invention for use in a method of preventing or treating retinal dystrophy.

In another related aspect, the invention provides the use of a vector of the invention in the manufacture of a medicament for the treatment or prevention of retinal dystrophy.

In another related aspect, the invention provides a method of treating or preventing retinal dystrophy in a patient in need thereof, comprising administering a therapeutically effective amount of a vector of the invention to said patient.

The invention also provides expression constructs and vectors comprising the promoters of the invention, as well as pharmaceutical compositions comprising such vectors, and the use of such vectors in treatment or prevention of retinal dystrophies, in particular disorders of the retinal pigment epithelium such as Leber congenital amaurosis.

BRIEF DESCRIPTION OF THE SEQUENCES

Figure 1:
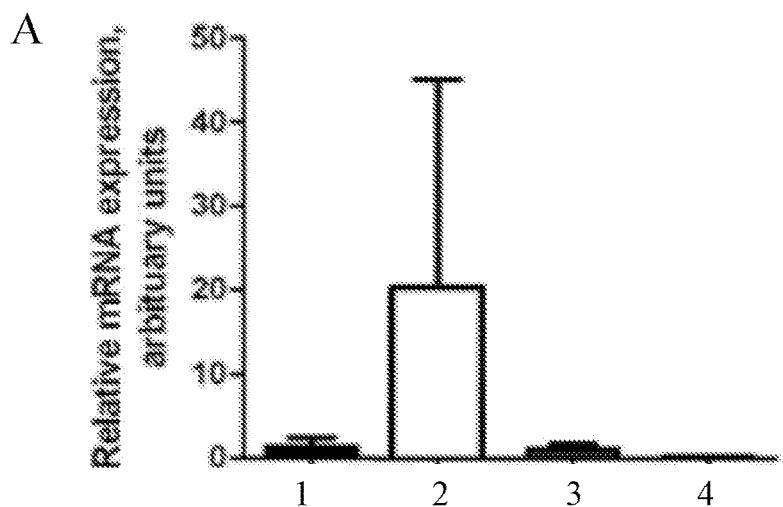
FIG. 1: GFP expression levels and pattern driven by original RPE65 promoter and new RPE65 promoter configurations in murine retinas following subretinal injection. Assessment of promoter activity using quantitative PCR (A) and protein blot (B). (C) Cryosections of eyes 4 weeks following subretinal injection of either AAV-RPE65-eGFP (top) or AAV-NA-eGFP (bottom).
Figure 1:
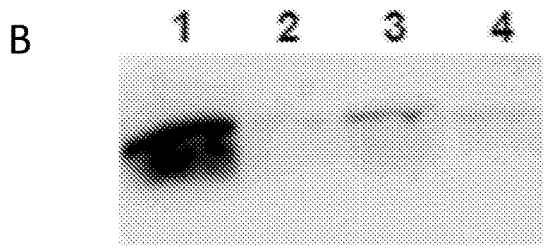
Figure 1:
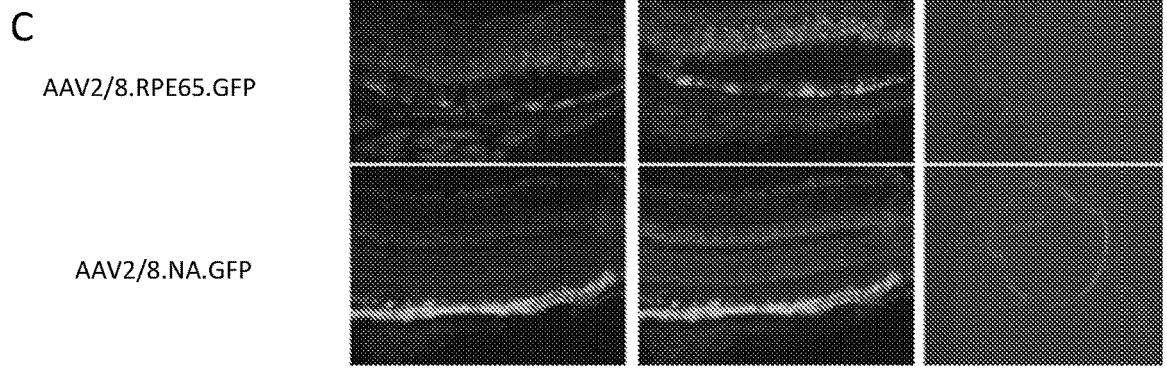

SEQ ID NO: 1 shows the DNA sequence of the human RPE65 promoter in the form used in Bainbridge et al (2008)
SEQ ID NO: 2 shows the DNA sequence of the optimised RPE65 promoter fragment
SEQ ID NO: 3 shows the native cDNA sequence of the human RPE65 gene
SEQ ID NO: 4 shows the cDNA sequence of the optimised RPE65 gene (Kozak sequence and coding sequence)
SEQ ID NO: 5 shows the cDNA sequence of the human MERTK gene
SEQ ID NO: 6 shows the cDNA sequence of the human LRAT gene
SEQ ID NO: 7 shows the cDNA sequence of the human TYR gene
SEQ ID NO: 8 shows the cDNA sequence of the human GRP143 gene
SEQ ID NOs: 9 and 10 show primer sequences that hybridise to RPE65
SEQ ID NOs: 11 and 12 show primer sequences that hybridise to eGFP
SEQ ID NOs:13 and 14 show primer sequences that hybridise to β-actin

DETAILED DESCRIPTION OF THE INVENTION

It is to be understood that different applications of the disclosed polynucleotide sequences may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural references unless the content clearly dictates otherwise. Thus, for example, reference to "a polynucleotide" includes "polynucleotides", reference to "a promoter" includes "promoters", reference to "a vector" includes two or more such vectors, and the like.

All publications, patents and patent applications cited herein, whether supra or infra, are hereby incorporated by reference in their entirety.

The present invention concerns gene therapy for the treatment and/or prevention of retinal dystrophy, in particular disorders of the retinal pigment epithelium such as Leber congenital amaurosis, in a patient.

The patient is preferably a mammal. The mammal may be a commercially farmed animal, such as a horse, a cow, a sheep or a pig, a laboratory animal, such as a mouse or a rat, or a pet, such as a cat, a dog, a rabbit or a guinea pig. The patient is more preferably human.

The promoters of the present invention can be used to treat retinal dystrophies. The retinal dystrophies may be inherited retinal dystrophies. Retinal dystrophy can be defined as a disease of the retina, characterised by progressive loss of photoreceptor cells and concomitant loss of vision.

The Retina

The retina is composed of the retinal pigment epithelium (RPE) cell layer and 3 layers of neurosensory cells; namely (from outer to inner), the outer nuclear layer (containing photoreceptor cells), the inner nuclear layer (containing bipolar cells), and the ganglion cell layer.

The Retinal Pigment Epithelium (RPE)

The RPE cells interdigitate with the photoreceptor outer segments. The space between the photoreceptors and the RPE cells contains a matrix through which compounds of the retinoid cycle move. The RPE has several noteworthy contributions to the function of the retina and the retinoid cycle. These include phagocytosis of photoreceptor outer segment discs, reduction of light scatter, contributing to the outer blood-retinal barrier, metabolism of vitamin A and maintenance of an immunosuppressive microenvironment (ocular immune privilege).

Retinal dystrophy or degeneration can be related to aberrations in the retinoid cycle. The retinoid cycle is the process by which the visual chromophores are regenerated. Photoisomerisation of the chromophore 11-cis-retinal creates all-trans-retinal, which, in turn, dissociates from rhodopsin. All-trans-retinal is then reduced to all-trans-retinol by the NADPH-dependent enzyme all-trans-retinol dehydrogenase (Baehr et al. 2003). All-trans-retinol subsequently leaves the photoreceptor cell, travels through the intercellular matrix and enters the RPE, wherein the final stages of pigment regeneration occur. Lecithin retinol acyltransferase (LRAT) esterifies all-trans-retinol to all-trans-retinyl ester. This is then converted into 11-cis-retinol by the RPE-predominant iron-dependent retinoid isomerohydrolase RPE65 ((Jin et al. 2005; Moiseyev et al. 2005; Redmond et al. 2005). The NAD- and NADP-dependent enzyme 11-cis-retinol dehydrogenase finally regenerates 11-cis-retinal through the oxidation of 11-cis-retinol. As such RPE65 protein is an essential component of the retinoid cycle.

Inherited Retinal Dystrophies of the RPE

Inherited retinal dystrophies of the RPE can include, amongst others, Leber congenital amaurosis, ocular albinism and MER proto-oncogene tyrosine kinase (MERTK) deficiency.

Leber Congenital Amaurosis (LCA)

Leber congenital amaurosis (LCA), one of the most severe forms of inherited retinal degeneration, is caused by autosomal recessive mutations in numerous genes, one of which is RPE65 (Gu et al., 1997; Marlhens et al. 1997; Morimura et al., 1998).

Leber congenital amaurosis (LCA) was first described by Theodor Karl Gustav Leber in 1869. It is a rare form of retinal degeneration, which accounts for a significant proportion of childhood blindness. Varying estimates of LCA incidence and prevalence are available from current data. For example, Alstrom and Olson estimated the worldwide prevalence of LCA to be 3 in 100,000 newborns (1957). A more recent analysis estimates LCA to be less prevalent, at 1 in 80,000 (Stone 2007). LCA is said to account for over 5% of all inherited retinopathies and roughly 20% of children attending schools for the blind worldwide (Schappert-Kimmijser et al. 1959). These statistics serve to illustrate the significant burden of morbidity inflicted by LCA, on both the individual and on society as a whole.

The clinical characteristics of LCA, first described by Leber in 1869, remain the primary criteria for the diagnosis today; namely, the quartet of severe visual loss at or near birth, wandering nystagmus (a form of involuntary eye movement), amaurotic pupils (a unresponsive pupil on the ipsilateral side to the affected eye, if the affected eye is stimulated by light), and pigmentary retinopathy (Ahmed and Loewenstein 2008; Koenekoop 2004; Leber 1869). In addition, the demonstration of absent electroretinographic (ERG) signals represents an absolute criterion for LCA diagnosis (den Hollander et al. 2008). Although often appreciated in retrospect (due to delayed diagnosis), one of the first clinical signs of LCA occurs in infants when they fail to track visually. This is, of course, a non-specific behavioural sign of severe visual impairment.

RPE Specific Genes Involved in LCA

RPE65

RPE65 is a retinyl ester-binding protein located primarily in the RPE cells. RPE65 is highly preferentially localised in the smooth endoplasmic reticulum of RPE cells, where the 11-cis-retinal chromophore is formed. Although the expression of RPE65 is relatively tissue-specific, RPE65 is also expressed in cone photoreceptors (Znoiko et al. 2002). RPE65 was originally shown to be a necessary component of the pathway by which 11-cis-retinol is regenerated from all-trans-retinyl ester (Gollapalli et al. 2003; Mata et al. 2004). It was hypothesised that RPE65 functioned as a substrate chaperone in this reaction.

However, subsequent studies have confirmed that RPE65 has an enzymatic role and represents the vital isomerohydrolase which recycles all-trans-retinoids to 11-cis-retinoids (Jin et al. 2005; Moiseyev et al. 2005; Redmond et al. 2005). The RPE65 isomerohydrolase activity was also found to be dependent upon $Fe^{2+}$, as mutations in $Fe^{2+}$-binding residues abolish its enzymatic activity (Moiseyev et al. 2006; Redmond et al. 2005). Mutations in the key enzymatic and iron-binding residues abolished this isomerohydrolase activity, caused accumulation of retinyl esters in the RPE, and blocked the retinoid cycle (Redmond et al. 1998; Redmond et al. 2005). There is also massive accumulation of all-trans-retinyl ester (the enzymatic substrate of RPE65), which appears as lipid droplets, in the murine RPE65−/− knockout model (Katz and Redmond 2001).

RPE65 mutations are responsible for a subtype of LCA (Gu et al., 1997; Marlhens et al. 1997; Morimura et al., 1998). Mutations in RPE65 are responsible for 6 to 16% of LCA cases and, in addition 2% of recessive Retinitis pigmentosa (RP) cases (Morimura et al. 1998; Hanein et al. 2004; Simonelli et al. 2007). Several studies have reported a higher prevalence of LCA-associated RPE65 mutations in the Mediterranean population compared to the rest of Europe and the United States (Hanein et al. 2004; Simonelli et al. 2007; Yzer et al. 2006).

Mutations in RPE65 are associated with several phenotypic features, including night blindness and the preservation of minimal visual function into the first decade of life (Simonelli et al. 2007). RPE65 mutations are also associated with a particular fundoscopic appearance; namely, salt-and-pepper retinal dystrophy (see FIG. 7; Stone 2007). In contrast to other LCA-associated mutations, such as those in CRB1, RPE65 mutations are associated with normal retinal thickness and detectable autofluorescence signals (Simonelli et al. 2007; Van Hooser et al. 2000).

The human RPE65 promoter region used in Bainbridge et al. 2008 is shown in SEQ ID NO:1. The human RPE65 cDNA sequence is shown in SEQ ID NO:3.

Lecithin Retinol Acyltransferase (LRAT)

Apart from RPE65, there are three other forms of severe retinal dystrophy caused by mutations in genes encoding proteins that function in the visual cycle—a set of biochemical reactions that regenerate visual pigment upon exposure to light. One of these, lecithin retinol acyltransferase (LRAT), is RPE-specific like RPE65. LRAT is the visual cycle enzyme that generates the substrate for RPE65, and defects in either result in virtually indistinguishable conditions. However, whereas the RPE65 gene is responsible for approximately 6% of all cases of LCA, mutations in LRAT only account for isolated cases of LCA. The cDNA sequence of human LRAT is shown in SEQ ID NO:6.

Ocular Albinism

Gene Involved in Ocular Albinism

Tyrosinase (TYR)

Tyrosinase (TYR) is the rate-limiting enzyme responsible for melanin biosynthesis in the RPE. Melanin has an important role in retinal development, function, and protection against light-induced oxidative stress, and melanin levels are associated with AMD. As well as being involved in AMD, mutations in Tyrosinase can also cause Oculo-cutaneous albinism type 1 (OCA1), which is characterised by congenital hypopigmentation.

Melanin can exert a protective function in tyrosinase-expressing cells in several ways. First, melanin shields these cells from the damage induced by sunlight and ultraviolet radiation. Second, melanin may counteract the oxidative stress caused by free radicals derived from lipid peroxidation products and accumulated iron in the RPE. Such prooxidants may contribute to age-related degeneration of this tissues. Third, the high binding capacity of melanin for metal ions and exogenous chemicals also lends support for a protective role of melanin in the eye. In concordance with these findings, melanin and its precursors are essential for the proper development of the retina in mammals. Malfunctions in normal expression of tyrosinase, its post-translational modification, or trafficking into melanosomes can decrease pigmentation, the stability of the melanosomes, and the normal functions of the RPE. Researchers have shown that the content of the RPE cells declines with age, perhaps in part due to oxidative degradation. In addition, several age-related changes occur in melanin, contributing to its functional decline. The cDNA sequence of human TYR is shown in SEQ ID NO:7.

G Protein-coupled Receptor 143 (GRP143)

GRP143 is expressed in the RPE. More than 60 G protein-coupled receptor 143 (GPR143) mutations have been identified in people with the most common form of ocular albinism, which is called the Nettleship-Falls type or type 1. The cDNA sequence of human GRP143 is shown in SEQ ID NO:8.

MER Proto-oncogene Tyrosine Kinase (MERTK) Deficiency

MERTK is a membrane tyrosine kinase that is expressed in RPE cells and is essential for normal phagocytosis of photoreceptor cell outer segments. Lack of functioning MERTK results in the accumulation of debris between the RPE and photoreceptor cells that adversely effects essential metabolic pathways.

In contrast to the photoreceptor cells, the RPE can be transduced efficiently with a variety of viral vectors and a number of studies have demonstrated improvements following gene supplementation of MERTK in the Royal College of Surgeons rat, which is a naturally occurring model of MERTK deficiency. The first of these studies used an adenovirus vector to transfer the Mertk gene to the RPE, leading to a short-term improvement in photoreceptor cell structure and function, as assessed by ERG. Subsequent studies have demonstrated that gene supplementation using AAV2 vector and HIV1-based lentiviral vectors can reduce deposition of debris, prolong photoreceptor cell survival and sustain ERG responses in the Royal College of Surgeons rats for up to 3 and 7 months, respectively. However, even lentiviral vector-mediated rescue, the most effective of the three vectors tested, has not prevented photoreceptor cell loss in the long term.

In the Royal College of Surgeons rats, the deficiency of MERTK compromises critical metabolic support, leading to a more rapid loss of cells. The cDNA sequence of human MERTK is shown in SEQ ID NO:5.

Age-related Macular Degeneration (AMD)

As well as inherited retinal dystrophies, the invention is also applicable to the treatment of AMD. Progressive retinal degenerative diseases, such as age-related macular degeneration (AMD) and retinitis pigmentosa (RP), are major causes of untreatable blindness and have a tremendous social and financial burden on society. As many as 30 million people worldwide are afflicted with AMD, and this diagnosis is expected to increase dramatically in the coming decades because of aging populations. AMD is an aging-associated multifactorial disease that affects the photoreceptor-RPE-choroid interface in the macula and is caused by the interaction of genetic susceptibility factors and environment. The RPE is the source and the target of many retinal degenerative diseases and defects in RPE function can affect the integrity and viability of neighbouring cells-primarily photoreceptors.

For the purposes of treating AMD, the coding sequence linked to the promoter of the invention will typically encode an anti-angiogenic polypeptide, for example sFlt1, sFlt-4, a VEGF-sequestering protein such as an antibody or antibody fragment that binds to VEGF, a soluble receptor for VEGF, angiostatin or endostatin; or a polypeptide with anti-apoptotic effects in the RPE, such as Bcl2 and other Bcl2 family members, XIAP (also known as BIRC4) and other IAP/BIRC family members.

Further Genes Suitable for Expression from Vectors of the Invention

Sequences that can be expressed from vectors of the invention for the purpose of correcting a range of ocular disorders also include genes encoding neurotrophic factors that support the survival of neurons, for example GDNF, CNTF, PEDF, VEGF, EPO, IGF1 and RdCVF1; anti-angiogenic polypeptides such as sFlt1, sFlt-4; a VEGF-seques- tering protein such as an antibody or antibody fragment that binds to VEGF, a soluble receptor for VEGF, angiostatin or endostatin; and sequences that encode polypeptides with anti-apoptotic effects in the RPE, such as Bcl2 and other Bcl2 family members, XIAP (also known as BIRC4) and other IAP/BIRC family members.

Neurotrophic factors that support the survival of neurons, for example GDNF, CNTF, PEDF, VEGF, EPO, IGF1 and RdCVF1 may be useful for the treatment of Stargardt disease.

Anti-angiogenic polypeptides such as sFlt1, sFlt-4; a VEGF-sequestering protein such as an antibody or antibody fragment that binds to VEGF, a soluble receptor for VEGF, angiostatin or endostatin; and sequences that encode polypeptides with anti-apoptotic effects in the RPE, such as Bcl2 and other Bcl2 family members, XIAP (also known as BIRC4) and other IAP/BIRC family members may be useful for the treatment of diabetic retinopathy.

Another gene that can be expressed from vectors of the invention is MYO7A, which is involved in the disease Usher 1B, which is thought to be partly caused by the absence of the protein encoded by MYO7A in the RPE.

Promoters of the Invention

The promoters of the invention are fragments and/or variants of the human RPE65 promoter and have RPE-specific promoter activity. They may be in isolated form.

A promoter of the invention may comprise a sequence of nucleotides, typically contiguous nucleotides, from SEQ ID NO:1 that confers RPE-specific expression on an operably linked polynucleotide sequence. The sequence of SEQ ID NO: 1 is 1614 nucleotides in length and does not have RPE-specific activity. Any truncation of SEQ ID NO: 1 that does have RPE-specific activity is a sequence of the invention. Promoter sequences of the invention may for example therefore comprise up to 1500 or 1600 nucleotides of SEQ ID NO: 1 but preferably they contain no more than 1300, no more than 1200, no more than 1100, no more than 1000, no more than 900, no more than 800, no more than 775, no more than 750, no more than 700, no more than 650, no more than 600 or no more than 500 nucleotides of SEQ ID NO: 1. Preferably, sequences of the invention however comprise at least 500, 550, 600, 650, 700, 750, 800, 900, 1000, 1100 or 1200 nucleotides of SEQ ID NO: 1. Preferably, the sequence of the invention is derived from the 3' end of SEQ ID NO: 1 and includes the 3' 500, 600, 650, 700, 750, 800, 900, 1000, 1100 or 1200 contiguous nucleotides of SEQ ID NO: 1, or lacks only up to 10, 20, 30, 40, 50, 60, 70, 80, 90, or 100 nucleotides of SEQ ID NO: 1.

Preferred promoters of the invention comprise the sequence of SEQ ID NO: 2 or the sequence of nucleotides 12-761 of SEQ ID NO:2 (nucleotides 1-11 of SEQ ID NO: 2 differ from the corresponding sequence of SEQ ID NO: 1; this is a cloning artefact whose presence does not detract from RPE-specific activity but is not necessary to it), typically within a sequence of no more than 800, no more than 850, no more than 900, no more than 1000, no more than 1100 or no more than 1200 contiguous nucleotides of SEQ ID NO: 1. Further preferred promoters comprise at least 750, at least 700, at least 650, at least 600, at least 550 or at least 500 contiguous nucleotides of SEQ ID NO: 2, preferably at least the 500, 550, 600, 650, 700 or 750 nucleotides that are at the 3' end of SEQ ID NO: 2 or at least the 550, 600, 650, 700 or 750 nucleotides that begin with nucleotide 12 of SEQ ID NO: 2.

Further promoters of the invention are promoters that differ in sequence from the sequences above but retain RPE-specific promoter activity. Such sequences have at least 75%, at least 80%, at least 85%, at least 90%, at least 95%, at least 98% or at least 99% sequence identity to a sequence of contiguous nucleotides from SEQ ID NO:1 as defined above.

Percentage sequence identity of variants is preferably measured over the full length of the corresponding portion of SEQ ID NO: 1, or over a 500, 600, 700, 800, 900, 1000, 1100 or 1200 nucleotide section of SEQ ID NO:1 aligned with the variant sequence.

Sequence identity may be calculated using any suitable algorithm. For example the PILEUP and BLAST algorithms can be used to calculate identity or line up sequences (such as identifying equivalent or corresponding sequences (typically on their default settings), for example as described in Altschul S. F. (1993) J Mol Evol 36:290-300; Altschul, S, F et al 25 (1990) J Mol Biol 215:403-10. Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of 30 the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate identity (for example used on its default settings) (Devereux et al (1984) Nucleic Acids Research 12, 387-395).

A promoter of the invention may also include additional nucleotide sequences not naturally found in the RPE65 promoter region. The promoter sequence of the invention may thus be positioned anywhere within a larger sequence as long as RPE 65-specific promoter activity is retained. The additional sequence can be 5' or 3', or both, to the sequence defined above.

The promoter of the invention can also be used in tandem with other regulatory elements such as one or more further promoters or enhancers or locus control regions (LCRs).

The promoters of the invention can be used to drive expression of genes in the RPE in an RPE-specific manner. RPE-specific expression may be defined as expression that is only present in the RPE, but not in other cell types. RPE-specific expression may be defined as expression that is more than about 10 times greater, 20 times greater, 50 times greater or 100 or more times greater in the RPE than in other cell types, especially photoreceptor cells. Expression in the RPE and other cells types can be measured by any suitable standard technique known to the person skilled in the art. For example, RNA expression levels can be measured by quantitative real-time PCR. Protein expression can be measured by western blotting or immunohistochemistry.

The promoters of the invention can be used to drive significantly increased expression of genes in the RPE. Significant increased expression can be defined as more than about 10 times, 20 times, 50 times, 100 times, 200 times or 300 times the expression of the gene in the RPE when compared with expression driven by the original RPE65 promoter (Bainbridge et al 2008). Expression in the RPE and other cells types can be measured by any suitable standard technique known to the person skilled in the art. For example, RNA expression levels can be measured by quantitative real-time PCR. Protein expression can be measured by western blotting or immunohistochemistry.

The promoters of the invention can be used to drive expression of any protein in the RPE. The promoters if the invention can be used to drive the expression of proteins which are not normally expressed in the RPE, in the RPE, such as GFP.

Expression Constructs

The present invention also provides expression constructs comprising the promoters of the invention operably linked to a sequence to be expressed in an RPE-specific manner.

An expression construct may be defined as a polynucleotide sequence capable of driving protein expression from a polynucleotide sequence containing a coding sequence.

Thus, the expression construct may for example comprise an RPE65, MERTK, LRAT, TYR or GRP143 coding sequence, for example a polynucleotide selected from SEQ ID NOs: 3 to 8, or a variant of SEQ ID NOs: 3 to 8 that retains the functionality of the protein translated from the sequence selected from SEQ ID NOs: 3 to 8.

A variant of a polynucleotide selected from the group consisting of SEQ ID NOs:3 to 8 may be defined as any variant of the sequence of SEQ ID NOs: 3 to 8, including naturally occurring variants in the nucleic acid sequence. The variant may be defined as having at least about 60%, 70%, 80%, 90%, 95%, 96%, 97%, 98% or 99% sequence identity to any one of SEQ ID NOs 3 to 8, wherein the polypeptide translated from the variant sequence retains its functionality. The variant may be defined as having at least about 60%, 70%, 80%, 90%, 95%, 96%, 97%, 98% or 99% sequence identity to any one of SEQ ID NOs 3 to 8, wherein the polypeptide translated from the variant sequence has the ability to rescue RPE function. Rescuing RPE function can be defined as rescuing at least about 50%, 60%, 70%, 80% 90%, 95%, 96%, 97%, 98%, 99% or 100% of RPE function. RPE function can be analysed by any suitable standard technique known to the person skilled in the art, for example, by electroretinography analysis of retinal responses.

The variant may be defined as having at least about 60%, 70%, 80%, 90%, 95%, 96%, 97%, 98% or 99% sequence identity to any one of SEQ ID NOs 3 to 8, wherein the resultant polypeptide translated from the variant sequence is the same as that translated from SEQ ID NOs:3 to 8.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the expression construct.

The expression construct may comprise a promoter of the invention operably linked to SEQ ID NO: 4.

"Codon optimization" relates to the process of altering a naturally occurring polynucleotide sequence to enhance expression in the target organism, for example, humans. In one embodiment of the present invention, the human RPE65 gene, SEQ ID NO: 3 has been optimised to create SEQ ID NO: 4. In the optimised RPE65 of SEQ ID NO: 4 seven rare codons (including a pair in tandem) have been replaced with those that occur more frequently and/or those which are frequently found in highly expressed human genes. In addition a cryptic splice site, 4 cryptic premature polyadenylation site and a direct repeat of 50 base pairs were removed.

Vectors

The present invention provides vectors comprising the promoters and expression constructs of the invention. The vector may be of any type, for example it may be a plasmid vector or a minicircle DNA.

Typically, vectors of the invention are however viral vectors. The viral vector may be based on the herpes simplex virus, adenovirus or lentivirus. The viral vector may be an adeno-associated virus (AAV) vector or a derivative thereof.

The viral vector derivative may be a chimeric, shuffled or capsid modified derivative.

The viral vector may comprise an AAV genome from a naturally derived serotype, isolate or clade of AAV.

The serotype may for example be AAV2, AAV5 or AAV8.

The efficacy of gene therapy is, in general, dependent upon adequate and efficient delivery of the donated DNA. This process is usually mediated by viral vectors. Adeno-associated viruses (AAV), a member of the parvovirus family, are commonly used in gene therapy. Wild-type AAV, containing viral genes, insert their genomic material into chromosome 19 of the host cell (Kotin, et al. 1990). The AAV single-stranded DNA genome comprises two inverted terminal repeats (ITRs) and two open reading frames, containing structural (cap) and packaging (rep) genes (Hermonat et al. 1984).

For therapeutic purposes, the only sequences required in cis, in addition to the therapeutic gene, are the ITRs. The AAV virus is therefore modified: the viral genes are removed from the genome, producing recombinant AAV (rAAV). This contains only the therapeutic gene, the two ITRs. The removal of the viral genes renders rAAV incapable of actively inserting its genome into the host cell DNA. Instead, the rAAV genomes fuse via the ITRs, forming circular, episomal structures, or insert into pre-existing chromosomal breaks. For viral production, the structural and packaging genes, now removed from the rAAV, are supplied in trans, in the form of a helper plasmid.

AAV is a particularly attractive vector as it is generally non-pathogenic; the majority people have been infected with this virus during their life with no adverse effects (Erles et al. 1999). Despite this, there are several drawbacks to the use of rAAV in gene therapy, although the majority of these only apply to systemic administration of rAAV. Nevertheless, it is important to acknowledge these potential limitations, even if not directly relevant to ocular administration of rAAV. Infection can trigger the following immunological responses:

As the majority of the human population is seropositive for AAV, neutralising antibodies against rAAV can impair gene delivery (Moskalenko et al. 2000; Sun et al. 2003).

Systemically delivered rAAV can trigger a capsid protein-directed T-cell response, leading to the apoptosis of transduced cells (Manno et al. 2006).

rAAV vectors can trigger complement activation (Zaiss et al. 2008).

As the rAAV delivery is generally unspecific, the vector can accumulate in the liver (Michelfelder et al. 2009).

The immune privilege of ocular tissue, a result of anatomical barriers and immunomodulatory factors, renders the eye largely exempt from the adverse immunological responses listed above (Taylor 2009).

AAV vectors are limited by a relatively small packaging capacity of roughly 4.8 kb and a slow onset of expression following transduction (Dong et al. 1996). Despite these minor drawbacks, AAV has become the most commonly used viral vector for retinal gene therapy.

Most vector constructs are based on the AAV serotype 2 (AAV2). AAV2 binds to the target cells via the heparin sulphate proteoglycan receptor (Summerford and Samulski 1998). The AAV2 genome, like those of all AAV serotypes, can be enclosed in a number of different capsid proteins. AAV2 can be packaged in its natural AAV2 capsid (AAV2/2) or it can be pseudotyped with other capsids (e.g. AAV2 genome in AAV1 capsid; AAV2/1, AAV2 genome in AAV5 capsid; AAV2/5 and AAV2 genome in AAV8 capsid; AAV2/8).

rAAV transduces cells via serotype specific receptor-mediated endocytosis. A major factor influencing the kinetics of rAAV transgene expression is the rate of virus particle uncoating within the endosome (Thomas et al. 2004). This, in turn, depends upon the type of capsid enclosing the genetic material (Ibid.). After uncoating the linear single-stranded rAAV genome is stabilised by forming a double-stranded molecule via de novo synthesis of a complementary strand (Vincent-Lacaze et al. 1999). The use of self-complementary DNA may bypass this stage by producing double-stranded transgene DNA. Natkunarajah et al. found that self-complementary AAV2/8 gene expression was of faster onset and higher amplitude, compared to single-stranded AAV2/8 (2008). Thus, by circumventing the time lag associated with second-strand synthesis, gene expression levels are increased, when compared to transgene expression from standard single-stranded constructs. Subsequent studies investigating the effect of self-complementary DNA in other AAV pseudotypes (e.g. AAV2/5) have produced similar results (Kong et al. 2010; Petersen-Jones et al. 2009). One caveat to this technique is that, as AAV has a packaging capacity of approximately 4.8 kb, the self-complementary recombinant genome must be appropriately sized (i.e. 2.3 kb or less).

In addition to modifying packaging capacity, pseudotyping the AAV2 genome with other AAV capsids can alter cell specificity and the kinetics of transgene expression. For example, when AAV2 is pseudotyped with the AAV4 capsid, transgene expression is targeted specifically to RPE cells (Le Meur et al. 2007). In addition, AAV2/8 is reported to transduce photoreceptors more efficiently than either AAV2/2 or AAV2/5 (Natkunaraj ah et al. 2008).

AAV Genome

The vector of the invention may comprise an adeno-associated virus (AAV) genome or a derivative thereof.

An AAV genome is a polynucleotide sequence which encodes functions needed for production of an AAV viral particle. These functions include those operating in the replication and packaging cycle for AAV in a host cell, including encapsidation of the AAV genome into an AAV viral particle. Naturally occurring AAV viruses are replication-deficient and rely on the provision of helper functions in trans for completion of a replication and packaging cycle. Accordingly and with the additional removal of the AAV rep and cap genes, the AAV genome of the vector of the invention is replication-deficient.

The AAV genome may be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype or isolate or clade of AAV. As is known to the skilled person, AAV viruses occurring in nature may be classified according to various biological systems.

Commonly, AAV viruses are referred to in terms of their serotype. A serotype corresponds to a variant subspecies of AAV which owing to its profile of expression of capsid surface antigens has a distinctive reactivity which can be used to distinguish it from other variant subspecies. Typically, a virus having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10 and AAV11, also recombinant serotypes, such as Rec2 and Rec3, recently identified from primate brain. In vectors of the invention, the genome may be derived from any AAV serotype. The capsid may also be derived from any AAV serotype. The genome and the capsid may be derived from the same serotype or different serotypes.

In vectors of the invention, it is preferred that the genome is derived from AAV serotype 2 (AAV2), AAV serotype 4 (AAV4), AAV serotype 5 (AAV5) or AAV serotype 8 (AAV8). It is most preferred that the genome is derived from AAV2 but other serotypes of particular interest for use in the invention include AAV4, AAV5 and AAV8, which efficiently transduce tissue in the eye, such as the retinal pigmented epithelium. It is preferred that the capsid is derived from AAV5 or AAV8.

Reviews of AAV serotypes may be found in Choi et al (*Curr Gene Ther.* 2005; 5(3); 299-310) and Wu et al (*Molecular Therapy.* 2006; 14(3), 316-327). The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV viruses may also be referred to in terms of clades or clones. This refers to the phylogenetic relationship of naturally derived AAV viruses, and typically to a phylogenetic group of AAV viruses which can be traced back to a common ancestor, and includes all descendants thereof. Additionally, AAV viruses may be referred to in terms of a specific isolate, i.e. a genetic isolate of a specific AAV virus found in nature. The term genetic isolate describes a population of AAV viruses which has undergone limited genetic mixing with other naturally occurring AAV viruses, thereby defining a recognisably distinct population at a genetic level.

Examples of clades and isolates of AAV that may be used in the invention include:

Clade A: AAV1 NC_002077, AF063497, AAV6 NC_001862, Hu. 48 AY530611, Hu 43 AY530606, Hu 44 AY530607, Hu 46 AY530609

Clade B: Hu. 19 AY530584, Hu. 20 AY530586, Hu 23 AY530589, Hu22 AY530588, Hu24 AY530590, Hu21 AY530587, Hu27 AY530592, Hu28 AY530593, Hu 29 AY530594, Hu63 AY530624, Hu64 AY530625, Hu13 AY530578, Hu56 AY530618, Hu57 AY530619, Hu49 AY530612, Hu58 AY530620, Hu34 AY530598, Hu35 AY530599, AAV2 NC_001401, Hu45 AY530608, Hu47 AY530610, Hu51 AY530613, Hu52 AY530614, Hu T41 AY695378, Hu S17 AY695376, Hu T88 AY695375, Hu T71 AY695374, Hu T70 AY695373, Hu T40 AY695372, Hu T32 AY695371, Hu T17 AY695370, Hu LG15 AY695377, Clade C: Hu9 AY530629, Hu10 AY530576, Hu11 AY530577, Hu53 AY530615, Hu55 AY530617, Hu54 AY530616, Hu7 AY530628, Hu18 AY530583, Hu15 AY530580, Hu16 AY530581, Hu25 AY530591, Hu60 AY530622, Ch5 AY243021, Hu3 AY530595, Hu1 AY530575, Hu4 AY530602 Hu2, AY530585, Hu61 AY530623

Clade D: Rh62 AY530573, Rh48 AY530561, Rh54 AY530567, Rh55 AY530568, Cy2 AY243020, AAV7 AF513851, Rh35 AY243000, Rh37 AY242998, Rh36 AY242999, Cy6 AY243016, Cy4 AY243018, Cy3 AY243019, Cy5 AY243017, Rh13 AY243013

Clade E: Rh38 AY530558, Hu66 AY530626, Hu42 AY530605, Hu67 AY530627, Hu40 AY530603, Hu41 AY530604, Hu37 AY530600, Rh40 AY530559, Rh2 AY243007, Bb1 AY243023, Bb2 AY243022, Rh10 AY243015, Hu11 AY530582, Hu6 AY530621, Rh25 AY530557, Pi2 AY530554, Pi1 AY530553, Pi3 AY530555, Rh57 AY530569, Rh50 AY530563, Rh49 AY530562, Hu39 AY530601, Rh58 AY530570, Rh61 AY530572, Rh52 AY530565, Rh53 AY530566, Rh51 AY530564, Rh64 AY530574, Rh43 AY530560, AAV8 AF513852, Rh8 AY242997, Rh1 AY530556

Clade F: Hu14 (AAV9) AY530579, Hu31 AY530596, Hu32 AY530597, Clonal Isolate AAV5 Y18065, AF085716, AAV 3 NC_001729, AAV 3B NC_001863, AAV4 NC_001829, Rh34 AY243001, Rh33 AY243002, Rh32 AY243003/

The skilled person can select an appropriate serotype, clade, clone or isolate of AAV for use in the present invention on the basis of their common general knowledge.

It should be understood however that the invention also encompasses use of an AAV genome of other serotypes that may not yet have been identified or characterised. The AAV serotype determines the tissue specificity of infection (or tropism) of an AAV virus. Accordingly, preferred AAV serotypes for use in AAV viruses administered to patients in accordance with the invention are those which have natural tropism for or a high efficiency of infection of target cells within the RPE.

Typically, the AAV genome of a naturally derived serotype or isolate or clade of AAV comprises at least one inverted terminal repeat sequence (ITR). Vectors of the invention typically comprise two ITRs, preferably one at each end of the genome. An ITR sequence acts in cis to provide a functional origin of replication, and allows for integration and excision of the vector from the genome of a cell. Preferred ITR sequences are those of AAV2 and variants thereof. The AAV genome typically comprises packaging genes, such as rep and/or cap genes which encode packaging functions for an AAV viral particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV viral particle. Capsid variants are discussed below.

Preferably the AAV genome will be derivatised for the purpose of administration to patients. Such derivatisation is standard in the art and the present invention encompasses the use of any known derivative of an AAV genome, and derivatives which could be generated by applying techniques known in the art. Derivatisation of the AAV genome and of the AAV capsid are reviewed in Coura and Nardi (*Virology Journal*, 2007, 4:99), and in Choi et al and Wu et al, referenced above.

Derivatives of an AAV genome include any truncated or modified forms of an AAV genome which allow for expression of a Rep-1 transgene from a vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences i.e. a self-complementary AAV genome. This allows for bypass of DNA replication in the target cell, and so enables accelerated transgene expression.

The one or more ITRs will preferably flank the expression construct cassette containing the promoter and transgene of the invention. The inclusion of one or more ITRs is preferred to aid packaging of the vector of the invention into viral particles. In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

With reference to the AAV2 genome, the following portions could therefore be removed in a derivative of the invention: One inverted terminal repeat (ITR) sequence, the replication (rep) and capsid (cap) genes. However, in some embodiments, including in vitro embodiments, derivatives may additionally include one or more rep and/or cap genes or other viral sequences of an AAV genome.

A derivative may be a chimeric, shuffled or capsid-modified derivative of one or more naturally occurring AAV viruses. The invention encompasses the provision of capsid protein sequences from different serotypes, clades, clones, or isolates of AAV within the same vector. The invention encompasses the packaging of the genome of one serotype into the capsid of another serotype i.e. pseudotyping.

Chimeric, shuffled or capsid-modified derivatives will be typically selected to provide one or more desired functionalities for the viral vector. Thus, these derivatives may display increased efficiency of gene delivery, decreased immunogenicity (humoral or cellular), an altered tropism range and/or improved targeting of a particular cell type compared to an AAV viral vector comprising a naturally occurring AAV genome, such as that of AAV2. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are cotransfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population.

The unrelated protein may also be one which assists purification of the viral particle as part of the production process i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al, referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The vector of the invention takes the form of a viral vector comprising the promoters and expression constructs of the invention.

For the avoidance of doubt, the invention also provides an AAV viral particle comprising a vector of the invention. The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral envelope. The AAV particle also includes chemically modified forms bearing ligands adsorbed to the capsid surface. For example, such ligands may include antibodies for targeting a particular cell surface receptor.

The invention additionally provides a host cell comprising a vector or AAV viral particle of the invention.

Preparation of Vector

The vector of the invention may be prepared by standard means known in the art for provision of vectors for gene therapy. Thus, well established public domain transfection, packaging and purification methods can be used to prepare a suitable vector preparation.

As discussed above, a vector of the invention may comprise the full genome of a naturally occurring AAV virus in addition to a promoter of the invention or a variant thereof. However, commonly a derivatised genome will be used, for instance a derivative which has at least one inverted terminal repeat sequence (ITR), but which may lack any AAV genes such as rep or cap.

In such embodiments, in order to provide for assembly of the derivatised genome into an AAV viral particle, additional genetic constructs providing AAV and/or helper virus functions will be provided in a host cell in combination with the derivatised genome. These additional constructs will typically contain genes encoding structural AAV capsid proteins i.e. cap, VP1, VP2, VP3, and genes encoding other functions required for the AAV life cycle, such as rep. The selection of structural capsid proteins provided on the additional construct will determine the serotype of the packaged viral vector.

A particularly preferred packaged viral vector for use in the invention comprises a derivatised genome of AAV2 in combination with AAV5 or AAV8 capsid proteins.

As mentioned above, AAV viruses are replication incompetent and so helper virus functions, preferably adenovirus helper functions will typically also be provided on one or more additional constructs to allow for AAV replication.

All of the above additional constructs may be provided as plasmids or other episomal elements in the host cell, or alternatively one or more constructs may be integrated into the genome of the host cell.

Promoter sequences of the invention have the ability to rescue loss of RPE function, which may occur for example by mutations in the RPE65 gene. "Rescue" generally means any amelioration or slowing of progression of a retinal dystrophy phenotype, for example restoring presence of RPE65 protein in the RPE, improving ERG activity or slowing loss of ERG activity, improving retinal sensitivity or slowing/halting progressive loss of retinal sensitivity, slowing or halting loss of photoreceptor cells, improving vision or slowing/halting vision loss.

The properties of promoters of the invention can also be tested using techniques based on those in the Examples. In particular, a sequence of the invention can be assembled into a vector of the invention and delivered to the retina of an to RPE65-deficient test animal, such as a mouse, and the effects observed and compared to a control. Preferably, the control will be the other eye of the same animal, which is either untreated or treated with a control vector such as one containing a reporter gene as opposed to a sequence of the invention. Electroretinography analysis of retinal responses to light can then be used to confirm that photoreceptor cells in the eyes that are treated with are more sensitive to light than photoreceptors from eyes that are untreated or treated with a control vector. The sensitivity of the treated eye to light may for example be at least 1.1, 1.2, 1.5, 2, 5, 10, 20, 50, 100, 200, 500 or 1000-fold greater than that of the untreated or control-treated eye.

Methods of Therapy and Medical Uses

The promoters of the invention may be used to treat retinal dystrophy, in particular LCA. This provides a means whereby the degenerative process of the disease can be treated, arrested, palliated or prevented.

The invention therefore provides a pharmaceutical composition comprising the vector of the invention and a pharmaceutically acceptable carrier.

The invention also provides a vector for use in a method of preventing or treating retinal dystrophy.

The invention also provides the use of a vector of the invention in the manufacture of a medicament for the treatment or prevention of retinal dystrophy.

The invention also provides a method of treating or preventing retinal dystrophy in a patient in need thereof comprising administering a therapeutically effective amount of a vector of the invention to the patient.

The invention also provides a method of treating or preventing retinal dystrophy in a patient in need thereof wherein the retinal dystrophy is Leber congenital amaurosis (LCA), age-related macular degeneration (AMD), oculocutaneous type 1, Nettleship-Falls type ocular albinism or MERTK deficiency.

According to the invention, in general treatment with RPE65 is preferred. More particularly, it is preferred that LCA will be treated with vectors that express an RPE65 or LRAT coding sequence, AMD with vectors that express genes whose expressed proteins suppress blood vessel growth or reduce or prevent RPE apoptosis, ocular albinism with a tyrosinase or GRP143 coding sequence and MERTK deficiency with a MERTK coding sequence.

In general, direct retinal, subretinal or intravitreal delivery of vectors of the invention, typically by injection, is preferred. Delivery to the retinal, subretinal space or intravitreal space is thus preferred.

The invention therefore also provides a method of treating or preventing retinal dystrophy in a patient in need thereof, comprising administering a therapeutically effective amount of a vector of the invention to the patient by direct retinal, subretinal or intravitreal injection. Accordingly, retinal dystrophy is thereby treated or prevented in said patient.

In a related aspect, the invention provides for use of a vector of the invention in a method of treating or preventing retinal dystrophy by administering said vector to a patient by direct retinal, subretinal or intravitreal injection. Additionally, the invention provides the use of a vector of the invention in the manufacture of a medicament for treating or preventing retinal dystrophy by direct retinal, subretinal or intravitreal injection.

The invention also provides a vector for use wherein said vector is administered directly into the retinal, subretinal space or intravitreal space.

In all these embodiments, the vector of the invention may be administered in order to prevent the onset of one or more symptoms of retinal dystrophy. The patient may be asymptomatic. The subject may have a predisposition to the disease. The method or use may comprise a step of identifying whether or not a subject is at risk of developing, or has, retinal dystrophy. A prophylactically effective amount of the vector is administered to such a subject. A prophylactically effective amount is an amount which prevents the onset of one or more symptoms of the disease.

Alternatively, the vector may be administered once the symptoms of the disease have appeared in a subject i.e. to cure existing symptoms of the disease. A therapeutically effective amount of the antagonist is administered to such a subject. A therapeutically effective amount is an amount which is effective to ameliorate one or more symptoms of the disease.

The subject may be male or female. The subject is preferably identified as being at risk of, or having, the disease.

The administration of the vector is typically by direct retinal or subretinal injection. This includes direct delivery to cells of the RPE. The delivery is made typically directly to or subretinally to the degenerating retina in a patient suffering from retinal dystrophy. The vector may transduce the above target cells without entering any other cell populations. Intravitreal injection may also be used to deliver the vector of the invention. The delivery may not be subretinal or may not be by subretinal injection. The delivery may not be transvitreal.

The dose of a vector of the invention may be determined according to various parameters, especially according to the age, weight and condition of the patient to be treated; the route of administration; and the required regimen. Again, a physician will be able to determine the required route of administration and dosage for any particular patient.

A typical single dose is between $10^{10}$ and $10^{12}$ genome particles, depending on the amount of remaining retinal tissue that requires transduction. A genome particle is defined herein as an AAV capsid that contains a single stranded DNA molecule that can be quantified with a sequence specific method (such as real-time PCR). That dose may be provided as a single dose, but may be repeated for the fellow eye or in cases where vector may not have targeted the correct region of retina for whatever reason (such as surgical complication). The treatment is preferably a single permanent treatment for each eye, but repeat injections, for example in future years and/or with different AAV serotypes may be considered.

Host Cells

Any suitable host cell can be used to produce the vectors of the invention. In general, such cells will be transfected mammalian cells but other cell types, e.g. insect cells, can also be used. In terms of mammalian cell production systems, HEK293 and HEK293T are preferred for AAV vectors. BHK or CHO cells may also be used.

Pharmaceutical Compositions and Dosages

The vector of the invention can be formulated into pharmaceutical compositions. These compositions may comprise, in addition to the vector, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may be determined by the skilled person according to the route of administration, i.e. here direct retinal, subretinal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

For injection at the site of affliction, the active ingredient will be in the form of an aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection, Hartmann's solution. Preservatives, stabilisers, buffers, antioxidants and/or other additives may be included, as required.

For delayed release, the vector may be included in a pharmaceutical composition which is formulated for slow release, such as in microcapsules formed from biocompatible polymers or in liposomal carrier systems according to methods known in the art.

Dosages and dosage regimes can be determined within the normal skill of the medical practitioner responsible for administration of the composition.

Combination Therapies

The promoters, expression constructs, vectors and/or pharmaceutical compositions can be used in combination with any other therapy for the treatment or prevention of retinal dystrophy.

Kits

The promoters, expression constructs, vectors and/or pharmaceutical compositions can be packaged into a kit.

EXAMPLES

Materials and Methods

Plasmid Constructions

To create fragments of the RPE65 promoter, the 'full length' human RPE65 promoter (bp 1556 to +23—Nicolletti et al. 1998, Le Meur et al. 2007) was cloned into the parent plasmid pD10.CMV.eGFP, creating pD10/RPE65prom.eGFP plasmid construct. Restriction sites were identified using CloneManager®. Three restriction modifications were selected, including: NsiI, AccI and BglII. pD10/RPE65prom.eGFP was digested at the appropriate temperature for at least 1 hour in appropriate buffers. Products were then run on a 0.8% gel for 40-60 mins, and the correct bands were extracted using NBS® Spin Column Gel Extraction Kit (NBS Biological Ltd, Cambridgeshire, UK), and ligated (post-blunting if necessary). Ligation products were transformed into *E. coli* (competent cells—Bioline) incubated for 30-60 minutes in Soc Media (Invitrogen), then plated on LB/Agar Ampicillin plates for overnight incubation at 37° C. Colonies were picked and grown in 12.5% LB medium (1/1000 Ampicillin) overnight. DNA was extracted from these bacterial preps using GenElute™ Plasmid Miniprep kit (Sigma Aldrich). DNA was digested at least twice to ascertain correct plasmid construct. Enzymes used to create new plasmid constructs were as follows: Nsi1 and Acc1 for 'NA-RPE65.eGFP', BglII for 'BglII-RPE65.eGFP'

For the optimised gene construct study, the pD10/CMV.SV40.kozak.RPE65opti was created by cloning the codon-, intron- and Kozak-optimised human RPE65 sequence from a pUC57 plasmid (produced by GenScript) into the CMV promoter-containing pD10plasmid pD10.CMV.eGFP (Sünkel-Laing and Buch, unpublished investigation). The 'full-length' RPE65 promoter was then cloned into the plasmid carrying the optimised construct.

Codon Optimization

Codon optimization was achieved through GenScript's proprietary OptimumGene™ codon optimization tool.

Virus Production Protocol AAV2/8

Recombinant AAV2 serotype 8 virus was produced using the triple transfection of 293T cells method previously described (Gao et el. 2002). 145 cm² plates of 293T cell plates (20 plates per virus batch) were transfected with a mix comprising of Plasmid of interest:Viral Capsid plasmid: Helper plasmid DNA in the ratio of 1:1:3, polyethylenimine (PEI—Polysciences Inc., Eppelheim, Germany) and DMEM after a 10 minute incubation. The transfected cells were bedded for 24 hours. 48 hours after transfection, cells were harvested, concentrated by centrifugation, resuspended in TD buffer (140 mMNaCl, 5 mMKCl, 0.7 mM $K_2HPO_4$, 3.5 mM $MgCl_2$, 25 mMTris Base [pH=7.5]). This was then lysed by 3-4 freeze-thaw cycles, followed by Benzonase (Sigma Aldrich, Dorset, UK) treatment, and then cellular debris was removed by successive centrifugation and syringe filtration steps.

Purification was performed by ion exchange chromatography (using a method based on that by Davidoff et al. 2004). The eluate was concentrated in a Vivaspin 4 10 kDa concentrator tube (Sartorius Stedim Biotech, Fisher Scientific, Loughborough, UK), washed in PBS-MK, then concentrated to a 100-150 μl volume, then aliquoted for −80° C. (long term) or +4° C. (short term) storage.

Transfection of 293 Ts

A 150 cm³ plate of HEK-293T cells was split into a 16-well plate. Each well was transfected using 0.5 μg of the desired plasmid DNA and 2 μg of PEI, and left to bed for ~60 hours. Cells were then harvested using the syringe plunger, then centrifuged at 14,000 rpm to pellet.

Immunohistochemistry

Eyes were prepared for fixation by corneal piercing, and then immersed in 1% paraformaldehyde (PFA, pH 7.4, using minute volumes of 0.07 M sodium cacodylate-HCl). Eyes were left to fix at room temperature for up to an hour, before being removed from solution, and fully immersed in Optimal cutting temperature (OCT) embedding matrix, with the anterior-posterior of the eye suspended in the horizontal-vertical axis within embedding tubes. These were then frozen and stored at −20° C. until required for sectioning.

13.5 micron coronal sections were prepared using Bright® OTF5000 Cryostat (Bright Instrument Co Ltd, Cambridgeshire, UK), thereby enabling the visualization of both the superior and inferior aspects of the retina. Slices were collected immediately after sectioning on polylysine-coated microscope slides, and allowed to air dry at room temperature. Slides were either stored at −20° C. or prepared for mounting in fluorescent mounting medium (DAKO). Slides were stained with DAPI either as an addition to the mounting medium (0.1% DAPI in medium) or by immersion in 0.2% DAPI in TBS and PBS-washing prior to mounted. Mounted slides were stored at 4° C.

Mounted slides were imaged using Zeiss AxioObserver Z1 (Carl Zeiss Inc, Gottingen, Germany). Pictures were taken at 2.5×, 10× and 20× magnification using appropriate fluorescence filters. GFP images were exposed at 200 ms and 5000 ms at magnifications of 10× and 20×, and at 9000 ms for 2.5× magnifications.

Tissue Dissection and RNA/Protein Extraction

Mice were sacrificed by cervical dislocation. Eyes were removed by pulling at the optic nerve, followed by a wash in PBS. The retina and RPE-choroid were carefully extracted by peeling, and immediately stored on ice in dry collection tubes for no more than 1 hour. Samples were processed using Qiagen® All-Prep DNA/RNA/Protein Kit. Note: the homogenisation step was carried out using the pestle-and-mortar technique.

RNA Extraction and Quantitative Real-Time PCR

RNA was eluted in 40 μl of RNAse-free $H_2O$, and stored immediately on ice or at −20° C. RNA concentration was quantified using Nanodrop® ND-1000 Spectrophotometer. Up to 1 μg of RNA (in each investigation the amount of used RNA corresponded to the sample containing the lowest amount of RNA within a given group of samples for comparison) was processed into cDNA using Qiagen® Quantitect® Reverse Transcription Kit. 1 μl of this was loaded into each well, along with a 29 μl volume of RT-PCR master mix; containing 50% 2× Bioline® Sensimix, 1.67% primer mix (both forward and reverse primers) in $dH_2O$. Each sample was loaded in triplicate. A standard logarithmic ladder of a plasmid construct containing the respective gene of interested was also loaded in parallel for absolute quantification. The PCR was run using standard conditions. Primers used include:

```
RPE65:
                                    (SEQ ID NO: 9)
5'-AATTACCAAATATTGTAAACGGTTCCATC-3', (SEQ ID NO: 10)
5'-TGTTTGAAACTGTGGAGGAACTGTC-3', eGFP:
                                    (SEQ ID NO: 11)
5'-GAAGCGCGATCACATGGT-3'
and (SEQ ID NO: 12)
5'-CCATGCCGAGAGTGATCC-3';

β-actin:
                                    (SEQ ID NO: 13)
5'-GTGGTACGACCAGAGGCATAC-3'
and (SEQ ID NO: 14)
5'-AAGGCCAACCGTGAAAAGAT-3'.
```

In all relative expression experiments, β-actin was used as a loading control. Data was analysed using One-way ANOVA using statistical software (GraphPad, PRISM).

Protein Extractions and Western Blots

Protein extracts were obtained using Qiagen® All-Prep DNA/RNA/Protein Kit, but resuspended and heat-treated at 95° C. in 100 μl 5% SDS in PBS containing protease inhibitor cocktail ((Sigma Aldrich, Gillingham, UK), then stored at −20° C. Prior to SDS-PAGE, protein concentrations were quantified using the Bio-Rad® Protein Assay (DC protein assay kit, Bio-Rad, Hemel Hempstead UK). Protein samples were made up to 20 μl with diluent, heatshocked at 95° C. with 4 µl loading dye, then loaded and run on a gel for SDS-PAGE for 120V for ~70 mins, bathed in 1× Tank Buffer (1.64% Tris base, 7.82% glycine, 0.54% SDS). 9% and 12% gels were utilised for RPE65 and GFP blots respectively. The electrophorised gel was then semi-dry transferred onto a PVDF membrane (Millipore Watford UK), then membrane blocked for an hour in 5% skimmed milk/1% BSA in PBS +0.05% Tween. Membranes were then blocked in primary antibody (α-GFP or α-RPE65), washed with PBS +0.05% Tween, then blocked with a 1:5,000-10, 000 dilution of secondary (HRP-conjugated) antibody (Pierce Immunopure goat anti-rabbit and goat anti-mouse IgG, Perbio Science UK Ltd., Northumberland UK). Washed blots were then immersed in ECL luminescence reagent (ECL plus GE Healthcare UK Ltd. Amersham, UK) then imaged using chemiluminescence detection (Fujifilm® LAS-1000 Luminescence Image Analyser). Densometric analysis was carried out this using ImageJ® software, and statistically analysed using non-parametric paired T-test.

Subretinal Injection

Subretinal injections were performed on Rd12 (Pang et al. 2005) and C57BL/6 mice at least 4 weeks after birth. An operating microscope was utilised throughout ophthalmic surgery. A 1.5 cm, 34-gauge hypodermic needle (Hamilton, Switzerland) was inserted tangentially through the sclera, creating a self-sealing scleral tunnel wound (Tan et al. 2009). 1.5-2.0 µl of the viral suspension was injected within the superior and inferior hemispheres of the subretinal space, each creating an ophthalmoscopically-visible bullous retinal detachment. C57BL/6 were utilised for the promoter study, and injected with $1 \times 10^{12}$ viral titre. Rd12 mice were used in the RPE65 rescue studies. Mice were injected with RPE65 viral constructs in a designated eye, with the RPE65opti viral constructs injected in the contralateral eye. Titres for 'low dose' (LD) experiments were $1 \times 10^9$ and $1 \times 10^{10}$ (two mice injected with each titre), and $1 \times 10^{11}$ vg/mL (viral genomes per milliliter) for all other rescue experiments. All mice were injected bilaterally.

In Vivo Treatment Efficacy

To compare the treatment efficacy of the optimised vector (AAV2/5-OptimisedRPE65) and the original vector (AAV2/2-hRPE65), Rpe65$^{-/-}$ mice were injected with AAV2/2-hRPE65 or with AAV2/5-optimisedRPE65 at titres ranging from $3 \times 10^7$ to $1 \times 10^9$ vg/mL (optimised construct) and from $1 \times 10^{10}$ to $1 \times 10^{12}$ vg/mL (original construct).

Figure 3:
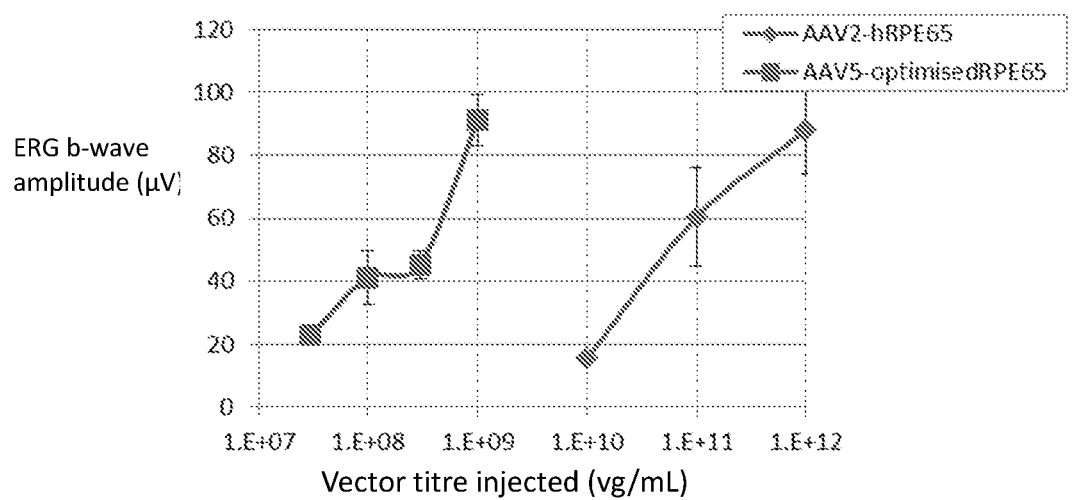
FIG. 3: Comparison of treatment efficacy of the optimised vector (AAV5-OptimisedRPE65) and the original vector (AAV2-hRPE65, Bainbridge et al 2008), 4 weeks post treatment. The graph shows average scotopic b-wave amplitudes (mean±SD) at 4 weeks post-treatment, when both vectors had reached peak expression. The optimised vector comprises the new (NA) RPE65 promoter configuration and the optimised RPE65 coding sequence.

Restoration of retinal function was assessed by electroretinography. The graph FIG. 3 shows average scotopic b-wave amplitudes (mean±SD) at 4 weeks post-treatment, when both vectors had reached peak expression. The b-wave amplitudes from the eyes treated with the optimised vector were as high as or higher than amplitudes from eyes injected with a 300-fold greater dose of the original vector. This demonstrates that the new vector is at least 300-fold more effective than the original vector. This assessment does not take into account the effect of codon optimisation, which does not lead to more efficient protein translation in the mouse.

Example 1: Optimisation of the Promoter Driving RPE Expression

As described in the "Plasmid Constructs" section above the 'full length' RPE65 promoter was digested with the NsiI and AccI restriction enzymes to create the "NA" RPE65 promoter fragment. This fragment is shown in SEQ ID NO:2. The 'full length' RPE65 promoter was also digested with the BglII restriction enzyme to create the "Bgl" promoter fragment. These promoter configurations (fragments of genomic DNA around the RPE65 transcription start site) were tested along side the 'full-length' promoter to determine the relative expression levels and the tissue specificity of expression. Assessments were done with the promoters driving GFP expression to facilitate localisation of transgene expression (FIG. 1). FIG. 1A shows Real-Time PCR analysis of GFP mRNA expression in RPE-choroid extracts, from AAV2/8 vectors harbouring the full-length RPE65 promoter "RPE65", or the "NA" or "Bgl" fragments. The "NA" fragment of the RPE65 promoter was effective with an expression level approximately 20× higher than the original RPE65 promoter (FIG. 1A). The "Bgl" fragment had no effect. For all values, p<0.05.

FIG. 1B shows a representative Western blot of GFP expression. The "NA" sample was diluted 1/20 in lane 2.

FIG. 1C shows thin cryosection fluorescent imaging of eyes injected with AAV2/8 vectors harbouring different promoters driving eGFP. Left panels show eGFP expression at 20× magnification, middle panels show co-staining with DAPI, right panels show eGFP expression at 2.5× magnification. The fluorescent images show that the optimised hRPE65 promoter was more potent than the normal hRPE65 promoter as well as more stringent in driving expression in RPE cells, as shown by eGFP intensity in the RPE and absence from the photoreceptors.

Example 2: Optimisation of the RPE65 cDNA

In order to attempt to improve the efficacy of post-transcriptional processing of the human RPE65 mRNA (RNA stability, nuclear export and translation) a number of modifications to the coding sequence of the RPE65 cDNA were made. This resulted in the sequence shown in SEQ ID NO:4. The Kozak sequence was optimised to "CCACCATG", see nucleotides 1 to 8 of SEQ ID NO:4, to attempt to achieve better recognition of the start codon and consequently more efficient translation. The natural Kozak sequence of the human RPE65 gene differed considerably from the obtained optimal consensus sequence.

Figure 2:
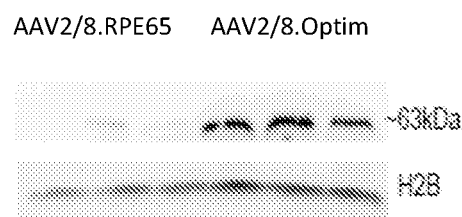
FIG. 2: Western blot assessment (A) and subsequent quantification (B) of in vitro RPE65 protein production in 293T cells after optimisation of the RPE65 coding sequence. The white bar shows RPE65 protein production using the unoptimised RPE65 coding sequence, the black bar shows RPE65 protein production using the optimised RPE65 coding sequence (SEQ ID NO:4).
Figure 2:
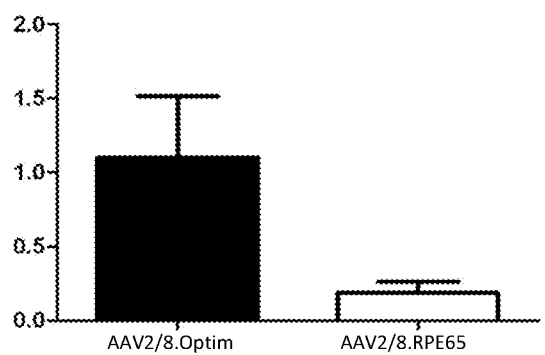

In addition, the coding sequence of RPE65 was subjected to codon optimisation, to attempt to improve the codon usage bias and CG content, and remove any cryptic processing sites and potential stem-loop structures in the mRNA. During optimisation of the RPE65 coding sequence 7 rare codons (including a pair in tandem), a cryptic splice site, 4 cryptic premature polyadenylation sites and a direct repeat of 50 base pairs were replaced. These changes significantly improved the codon usage frequency. These changes were tested together in vitro in (human) 293T cells to determine their effect on RPE65 protein production levels, after transfection of an AAV2/8 expression plasmid carrying the ubiquitous CMV promoter (FIG. 2). FIG. 2A shows a Western blot of RPE65 expression. FIG. 2B shows a quantification of the Western Blot. In vitro protein production in 293T cells after optimisation of the RPE65 coding sequence showed a seven-fold increase in the amount of RPE65 protein produced from the vector carrying the optimised coding sequence (AAV2/8.Optim) compared to the wild type coding sequence (AAV2/8.RPE65) (p<0.05).

Example 3: In Vivo Assessment of Treatment Efficacy

A construct consisting of the promoter that resulted in the highest level of expression, the "NA" fragment shown in SEQ ID NO:2, and the optimised RPE65 coding sequence shown in SEQ ID NO:4, was packaged in AAV5 and AAV8 capsids and tested for its ability to rescue retinal function in vivo in RPE65-deficient mice. Efficacy of rescue was compared against the clinical grade vector previously used in Bainbridge et al (2008), "AAV2-hRPE65". This vector contained the human RPE65 coding sequence driven by a 1400-bp fragment of the human RPE65 promoter. As the previous vector already led to rescue in animals, lower vector doses were administered to allow comparison of treatment efficacy under limiting circumstances (FIG. 3). b-wave amplitude was used as a measure of rescue. Surprisingly, the b-wave amplitudes from the eyes treated with the optimised vector were as high as or higher than amplitudes from eyes injected with a 300-fold higher dose of the original vector. This showed that the new vector was at least 300-fold more effective than the original vector.

REFERENCES

Ahmed, E. and Loewenstein, J., Leber congenital amaurosis: disease, genetics and therapy, *Semin. Ophthalmol.* 23, 39-43 (2008).
Alstrom, C. H. and Olson O., Heredo-retinopathia cengetalis monohybrida recessive autosomalis. A genetical statistical study, *Hereditas*, 43, 178 (1957).
Altschul S. F. A protein alignment scoring system sensitive at all evolutionary distances *J. Mol. Evol.* 36, 290-300 (1993).
Altschul, S. F. et al., Basic local alignment search tool *J. Mol. Biol.*, 215, 403-410 (1990).
Ashtari, M. et al., The human visual cortex responds to gene therapy-mediated recovery of retinal function, *J. Clin. Invest.* 121, 2160-2168 (2011).
Baehr, W. et al., The visual cycle and retina disease, *Vision Res.* 43, 2957-2958 (2003).
Bainbridge, J. W. B. et al., Effect of gene therapy on visual function in Leber's congenital amaurosis, *N. Engl. J. Med.* 358, 2231-2239 (2008).
Choi, V. W. et al., AAV hybrid serotypes: improved vectors for gene delivery, *Curr. Gene Ther.*, 5, 299-310 (2005).
Cideciyan, A. V. et al., Human gene therapy for RPE65 isomerase deficiency activates the retinoid cycle of vision but with slow rod kinetics, *Proc. Natl. Acad. Sci. U.S.A* 105, 15112-15117 (2008).
Cideciyan, A. V. et al., Vision 1 year after gene therapy for Leber's congenital amaurosis, *N. Engl. J. Med.* 361, 725-727 (2009).
Coura Rdos S. and Nardi, N. B., The state of the art of adeno-associated virus-based vectors in gene therapy, *Virol. J.*, 4, 99 (2007).
Davidoff, A. M. et al., Purification of recombinant adeno-associated virus type 8 vectors by ion exchange chromatography generates clinical grade vector stock *J. Virol. Meth.* 121, 209-215 (2004).
den Hollander, A. I. et al., Leber congenital amaurosis: genes, proteins and disease mechanisms, *Prog. Retin. Eye Res.* 27, 391-419 (2008).
Devereux, J. et al. A comprehensive set of sequence analysis programmes for the VAX. *Nucl. Acids Res.* 12, 387-395 (1984).
Dong, J. Y. et al., Quantitative analysis of the packaging capacity of recombinant adeno-associated virus, *Hum. Gene Ther.*, 7, 2101-2112 (1996).
Erles, K., Sebokova, P. and Schlehofer, J. R., Update on the prevalence of serum antibodies (IgG and IgM) to adeno-associated virus (AAV), *J. Med. Virol.* 59, 406-411 (1999).
Gao, G. P. et al., Novel adeno-associated viruses from rhesus monkeys as vectors for human gene therapy, *Proc. Natl. Acad. Sci U.S.A* 99, 11854-11859 (2002).
Gollapalli, D. R. et al., RPE65 operates in the vertebrate visual cycle by stereospecifically binding all-trans-retinyl esters, *Biochemistry*, 42, 11824-11830 (2003).
Gu, S. M. et al., Mutations in RPE65 cause autosomal recessive childhood-onset severe retinal dystrophy, *Nat. Genet.* 17, 194-197 (1997).
Hanein, S. et al., Leber congenital amaurosis: comprehensive survey of the genetic heterogeneity, refinement of the clinical definition, and genotype-phenotype correlations as a strategy for molecular diagnosis, *Hum. Mutat.* 23, 306-317 (2004).
Hauswirth, W. et al., Phase I Trial of Leber Congenital Amaurosis due to RPE65 Mutations by Ocular Subretinal Injection of Adeno-Associated Virus Gene Vector: Short-Term Results, *Hum. Gene Ther.* 19, 979-990 (2008).
Henikoff, S. and Henikoff, J. G., *Proc. Natl. Acad. Sci. USA* 89, 10915-10919 (1992).
Hermonat, P. L. et al., Genetics of adeno-associated virus: isolation and preliminary characterization of adeno-associated virus type 2 mutants, *J. Virol.*, 51, 329-339 (1984).
Jin, M. et al., Rpe65 is the retinoid isomerase in bovine retinal pigment epithelium, *Cell*, 122, 449-459 (2005).
Karlin, S. and Altschul, S. F., Applications and statistics for multiple high-scoring segments in molecular sequences Proc. Natl. Acad. Sci. USA 90: 5873-5787 (1993).
Katz, M. L. and Redmond, T. M., Effect of Rpe65 knockout on accumulation of lipofuscin fluorophores in the retinal pigment epithelium, *Invest. Ophthalmol. Vis. Sci.*, 42., 3023-3030 (2001).
Koenekoop, R. K., An overview of Leber congenital amaurosis: a model to understand human retinal development, *Surv. Ophthalmol* 49, 379-398 (2004).
Kong, F. et al., Self-complementary AAV5 vector facilitates quicker transgene expression in photoreceptor and retinal pigment epithelial cells of normal mouse, *Exp. Eye Res.*, 90, 546-554 (2010).
Kotin, R. M. et al., Site-specific integration by adeno-associated virus, *Proc. Natl. Acad. Sci U.S.A* 87, 2211-2215 (1990).
Leber, T., Über retinitis pigmentosa und angeborene Amaurose, *Graefes Arch. Augenheilk.* 15, 1 (1859).
Le Meur, G. et al., Restoration of vision in RPE65-deficient Briard dogs using an AAV serotype 4 vector that specifically targets the retinal pigmented epithelium, 14, 292-303 (2007).
Maguire, A. M. et al., Safety and efficacy of gene transfer for Leber's congenital amaurosis, *N. Engl. J. Med.* 358, 2240-2248 (2008).
Maguire, A. M. et al., Age-dependent effects of RPE65 gene therapy for Leber's congenital amaurosis; a phase 1 dose-escalation trial. *The Lancet* 374, 1597-1605 (2009).
Manno, C. S. et al., Successful transduction of liver in hemophilia by AAV-Factor IX and limitations imposed by the host immune response, *Nat. Med.* (2006).
Marlhens, F. et al., Mutations in RPE65 cause Leber's congenital amaurosis, *Nat. Genet.* 17, 139-141 (1997).
Mata, N. L. et al., Rpe65 is a retinyl ester binding protein that presents insoluble substrate to the isomerase in retinal pigment epithelial cells, *J. Biol. Chem.*, 279, 635-643 (2004).
Michelfelder, S. and Trepel, M., Adeno-associated viral vectors and their redirection to cell-type specific receptors, *Adv. Genet.*, 67, 29-60 (2009).

Moiseyev, G. et al., RPE65 is the isomerohydrolase in the retinoid visual cycle, *Proc. Natl. Acad. Sci. U.S.A* 102, 12413-12418 (2005).
Morimura, H. et al., Mutations in the RPE65 gene in patients with autosomal recessive retinitis pigmentosa or leber congenital amaurosis, *Proc. Natl. Acad. Sci. U.S.A* 95, 3088-3093 (1998).
Moskalenko, M. et al., Epitope mapping of human anti-adeno-associated virus type 2 neutralizing antibodies: implications for gene therapy and virus structure, *J. Virol.*, 74, 1761-1766 (2000).
Natkunaraj ah, M. et al., Assessment of ocular transduction using single-stranded and self-complementary recombinant adeno-associated virus serotype 2/8, *Gene Ther.* 15, 463-467 (2008).
Nicolletti, A. et al., Promoter analysis of RPE65, the gene encoding a 61-kDa retinal pigment epithelium-specific protein, *Invest. Ophthalmol. Vis. Sci.*, 39, 637-644 (1998).
Pang, J. J. et al., Retinal degeneration 12 (rd12): a new, spontaneously arising mouse model for human Leber congenital amaurosis (LCA), Mol. Vis 11, 152-162 (2005).
Petersen-Jones, S. M. et al., AAV retinal transduction in a large animal model species: comparison of a self-complementary AAV2/5 with a single-stranded AAV2/5 vector, *Mol. Vis.*, 15, 1835-1842 (2009).
Redmond, T. M. et al., Mutation of key residues of RPE65 abolishes its enzymatic role as isomerohydrolase in the visual cycle, *Proc. Natl. Acad. Sci. U.S.A* 102, 13658-13663 (2005).
Redmond, T. M. et al., Rpe65 is necessary for production of 11-cis-vitamin a in the retinal visual cycle. *Nat Genet.* 20, 344-351 (1998).
Schappert-Kimmijser, J. et al., Amaurosis congenita (Leber), *AMA Arch. Ophthalmol.* 61, 211-218 (1959).
Simonelli, F. et al., Clinical and molecular genetics of Leber's congenital amaurosis: a multicenter study of Italian patients, *Invest. Ophthalmol. Vis. Sci.*, 48, 4284-4290 (2007).
Stone, E. M., Genetic testing for inherited eye disease, *Arch. Ophthalmol.*, 125, 205-212 (2007).
Summerford, C. and Samulski, R. J., Membrane-associated heparan sulfate proteoglycan is a receptor for adeno-associated virus type 2 virions, *J. Virol.*, 72, 1438-1445 (1998).
Sun, J. Y. et al., Immune responses to adeno-associated virus and its recombinant vectors, 10, 964-976 (2003).
Tan, M. H. et al., Gene therapy for retinitis pigmentosa and Leber congenital amaurosis caused by defects in AIPL1: effective rescue of mouse models of partial and complete Aipl1 deficiency using AAV2/2 and AAV2/8 vectors, *Hum. Mol. Genet.* 18, 2099-2114 (2009).
Taylor, A. W., Ocular immune privilege, *Eye*, 23, 1885-1889 (2009).
Thomas, C. E. et al., Rapid uncoating of vector genomes is the key to efficient liver transduction with pseudotyped adeno-associated virus vectors, *J. Virol.* 78, 3110-3122 (2004).
Van Hooser, J. P. et al., Rapid restoration of visual pigment and function with oral retinoid in a mouse model of childhood blindness, *Proc. Natl. Acad. Sci. U.S.A* 97, 8623-8628 (2000).
Vincent-Lacaze, N. et al., Structure of adeno-associated virus vector DNA following transduction of the skeletal muscle, *J Virol.* 73, 1949-1955 (1999).
Wu, Z. et al., Adeno-associated virus serotypes: vector toolkit for human gene therapy, *Mol. Ther.*, 14, 316-327 (2006).
Yzer, S. et al., Microarray-based mutation detection and phenotypic characterization of patients with Leber congenital amaurosis, *Invest Ophthalmol. Vis. Sci.* 47, 1167-1176 (2006).
Zaiss, A. K. and Muruve, D. A., Immunity to adeno-associated virus vectors in animals and humans: a continued challenge. *Gene Ther* 15, 808-816 (2008).
Znoiko, S. L. et al., Identification of the RPE65 protein in mammalian cone photoreceptors, *Invest. Ophthalmol. Vis. Sci.*, 43, 1604-1609 (2002).

SEQUENCE INFORMATION

Boxed sequence in SEQ ID NO:1 shows the nucleotides of SEQ ID NO:1 that were removed in SEQ ID NO:2 and their position. Boxed sequence in SEQ ID NO: 2 shows the nucleotides that were added in the place of those removed from the box shown in SEQ ID NO: 1. Bold and underlined text in SEQ ID NO: 1 and 2 shows the relative position of the beginning of SEQ ID NO: 2.

```
RPE65 promoter region Genbank No. NG_008472.1
                                                              SEQ ID NO: 1
TATTGTGCAAATAAGTGCTCACTCCAAATTAGTGGTATATTTATTGAAGTTTAATATTGTGTTTGTGATACAGAA

GTATTTGCTTTAATTCTAAATAAAAATTTTATGCTTTTATTGCTGGTTTAAGAAGATTTGGATTATCCTTGTACT

TTGAGGAGAAGTTTCTTATTTGAAATATTTTGGAAACAGGTCTTTTAATGTGGAAAGATAGATATTAATCTCCTC

TTCTATTACTCTCCAAGATCCAACAAAAGTGATTATACCCCCCAAAATATGATGGTAGTATCTTATACTACCATC

ATTTTATAGGCATAGGGCTCTTAGCTGCAAATAATGGAACTAACTCTAATAAAGCAGAACGCAAATATTGTAAAT

ATTAGAGAGCTAACAATCTCTGGGATGGCTAAAGGATGGAGCTTGGAGGCTACCCAGCCAGTAACAATATTCCGG

GCTCCACTGTTGAATGGAGACACTACAACTGCCTTGGATGGGCAGAGATATTATGGATGCTAAGCCCCAGGTGCT

ACCATTAGGACTTCTACCACTGTCCCTAACGGGTGGAGCCCATCACATGCCTATGCCCTCACTGTAAGGAAATGA

AGCTACTGTTGTATATCTTGGGAAGCACTTGGATTAATTGTTATACAGTTTTGTTGAAGAAGACCCCTAGGGTAA

GTAGCCATAACTGCACACTAAATTTAAAATTGTTAATGAGTTTCTCAAAAAAAATGTTAAGGTTGTTAGCTGGTA

TAGTATATATCTTGCCTGTTTTCCAAGGACTTCTTTGGGCAGTACCTTGTCTGTGCTGGCAAGCAACTGAGACTT

AATGAAAGAGTATTGGAGATATGAATGAATTGATGCTGTATACTCTCAGAGTGCCAAACATATACCAATGGACAA
```

GAAGGTGAGGCAGAGAGCAGACAGGCATTAGTGACAAGCAAAGATATGCAGAATTTCATTCTCAGCAAATCAAAA

GTCCTCAACCTGGTTGGAAGAATATTGGCACTGAATGGTATCAATAAGGTTGCTAGAGAGGGTTAGAGGTGCACA

ATGTGCTTCCATAACATTTTATACTTCTCCAATCTTAGCACTAATCAAACATGGTTGAATACTTTGTTTACTATA

ACTCTTACAGAGTTATAAGATCTGTGAAGACAGGGACAGGGACAATACCCATCTCTGTCTGGTTCATAGGTGGTA

TGTAATAGATATTTTTAAAAATAAGTGAGTTAATGAATGAGGGTGAGAATGAAGGCACAGAGGTATTAGGGGGAG

GTGGGCCCCAGAGAATGGTGCCAAGGTCCAGTGGGGTGACTGGGATCAGCTCAGGCCTGACGCTGGCCACTCCCA

CCTAGCTCCTTTCTTTCTAATCTGTTCTCATTCTCCTTGGGAAGGATTGAGGTCTCTGGAAAACAGCCAAACAAC

TGTTATGGGAACAGCAAGCCCAAATAAAGCCAAGCATCAGGGGGATCTGAGAGCTGAAAGCAACTTCTGTTCCCC

CTCCCTCAGCTGAAGGGGTGGGGAAGGGCTCCCAAAGCCATAACTCCTTTTAAGGGATTTAGAAGGCATAAAAAG

GCCCCTGGCTGAGAACTTCCTTCTTCATTCTGCAGTTGG

Optimised RPE65 promoter fragment
SEQ ID NO: 2
AGATCTTCGAAATACTCTCAGAGTGCCAAACATATACCAATGGACAAGAAGGTGAGGCAGAGAGCAGACAGGCAT

TAGTGACAAGCAAAGATATGCAGAATTTCATTCTCAGCAAATCAAAGTCCTCAACCTGGTTGGAAGAATATTGG

CACTGAATGGTATCAATAAGGTTGCTAGAGAGGGTTAGAGGTGCACAATGTGCTTCCATAACATTTTATACTTCT

CCAATCTTAGCACTAATCAAACATGGTTGAATACTTTGTTTACTATAACTCTTACAGAGTTATAAGATCTGTGAA

GACAGGGACAGGGACAATACCCATCTCTGTCTGGTTCATAGGTGGTATGTAATAGATATTTTTAAAAATAAGTGA

GTTAATGAATGAGGGTGAGAATGAAGGCACAGAGGTATTAGGGGGAGGTGGGCCCCAGAGAATGGTGCCAAGGTC

CAGTGGGGTGACTGGGATCAGCTCAGGCCTGACGCTGGCCACTCCCACCTAGCTCCTTTCTTTCTAATCTGTTCT

CATTCTCCTTGGGAAGGATTGAGGTCTCTGGAAAACAGCCAAACAACTGTTATGGGAACAGCAAGCCCAAATAAA

GCCAAGCATCAGGGGGATCTGAGAGCTGAAAGCAACTTCTGTTCCCCCTCCCTCAGCTGAAGGGGTGGGGAAGGG

CTCCCAAAGCCATAACTCCTTTTAAGGGATTTAGAAGGCATAAAAAGGCCCCTGGCTGAGAACTTCCTTCTTCAT

TCTGCAGTTGG cDNA of human RPE65 Genbank No. NM_000329.2
SEQ ID NO: 3
ATGTCTATCCAGGTTGAGCATCCTGCTGGTGGTTACAAGAAACTGTTTGAAACTGTGGAGGAACTGTCCTCGCCG

CTCACAGCTCATGTAACAGGCAGGATCCCCCTCTGGCTCACCGGCAGTCTCCTTCGATGTGGGCCAGGACTCTTT

GAAGTTGGATCTGAGCCATTTTACCACCTGTTTGATGGGCAAGCCCTCCTGCACAAGTTTGACTTTAAAGAAGGA

CATGTCACATACCACAGAAGGTTCATCCGCACTGATGCTTACGTACGGGCAATGACTGAGAAAAGGATCGTCATA

ACAGAATTTGGCACCTGTGCTTTCCCAGATCCCTGCAAGAATATATTTTCCAGGTTTTTTTCTTACTTTCGAGGA

GTAGAGGTTACTGACAATGCCCTTGTTAATGTCTACCCAGTGGGGGAAGATTACTACGCTTGCACAGAGACCAAC

TTTATTACAAAGATTAATCCAGAGACCTTGGAGACAATTAAGCAGGTTGATCTTTGCAACTATGTCTCTGTCAAT

GGGGCCACTGCTCACCCCCACATTGAAAATGATGGAACCGTTTACAATATTGGTAATTGCTTTGGAAAAAATTTT

TCAATTGCCTACAACATTGTAAAGATCCCACCACTGCAAGCAGACAAGGAAGATCCAATAAGCAAGTCAGAGATC

GTTGTACAATTCCCCTGCAGTGACCGATTCAAGCCATCTTACGTTCATAGTTTTGGTCTGACTCCCAACTATATC

GTTTTTGTGGAGACACCAGTCAAATTAACCTGTTCAAGTTCCTTTCTTCATGGAGTCTTTGGGGAGCCAACTAC

ATGGATTGTTTTGAGTCCAATGAAACCATGGGGGTTTGGCTTCATATTGCTGACAAAAAAGGAAAAGTACCTC

AATAATAAATACAGAACTTCTCCTTTCAACCTCTTCCATCACATCAACACCTATGAAGACAATGGGTTTCTGATT

GTGGATCTCTGCTGCTGGAAAGGATTTGAGTTTGTTTATAATTACTTATATTTAGCCAATTTACGTGAGAACTGG

GAAGAGGTGAAAAAAAATGCCAGAAAGGCTCCCCAACCTGAAGTTAGGAGATATGTACTTCCTTTGAATATTGAC

AAGGCTGACACAGGCAAGAATTTAGTCACGCTCCCCAATACAACTGCCACTGCAATTCTGTGCAGTGACGAGACT

ATCTGGCTGGAGCCTGAAGTTCTCTTTTCAGGGCCTCGTCAAGCATTTGAGTTTCCTCAAATCAATTACCAGAAG

TATTGTGGGAAACCTTACACATATGCGTATGGACTTGGCTTGAATCACTTTGTTCCAGATAGGCTCTGTAAGCTG

AATGTCAAAACTAAAGAAACTTGGGTTTGGCAAGAGCCTGATTCATACCCATCAGAACCCATCTTTGTTTCTCAC

CCAGATGCCTTGGAAGAAGATGATGGTGTAGTTCTGAGTGTGGTGGTGAGCCCAGGAGCAGGACAAAAGCCTGCT

TATCTCCTGATTCTGAATGCCAAGGACTTAAGTGAAGTTGCCCGGGCTGAAGTGGAGATTAACATCCCTGTCACC

TTTCATGGACTGTTCAAAAAATCTTGA

Optimised RPE65 cDNA (Kozak sequence and coding sequence)

SEQ ID NO: 4

CCACCATGAGTATCCAGGTGGAACATCCCGCAGGGGGGTATAAGAAACTGTTTGAGACCGTCGAAGAACTGAGCA

GCCCTCTGACCGCACATGTCACCGGAAGAATCCCCCTGTGGCTGACAGGATCACTGCTGAGATGCGGACCAGGAC

TGTTCGAAGTGGGAAGCGAACCTTTCTACCACCTGTTTGACGGACAGGCCCTGCTGCATAAGTTCGACTTCAAGG

AGGGGCACGTGACTTACCATCGGCGGTTCATCCGAACCGACGCCTATGTCCGGGCTATGACAGAGAAGAGAATCG

TGATTACTGAGTTCGGCACCTGCGCCTTTCCAGATCCCTGTAAGAACATTTTCTCCAGGTTCTTTTCTTACTTTC

GCGGCGTCGAGGTGACAGACAACGCACTGGTCAACGTGTACCCTGTGGGGAGGATTACTATGCCTGCACTGAAA

CCAACTTCATCACCAAGATTAATCCAGAGACACTGGAAACTATCAAACAGGTGGACCTGTGCAACTACGTCAGTG

TGAATGGCGCCACCGCTCACCCCCATATCGAGAACGATGGGACAGTCTACAACATTGGCAATTGCTTCGGGAAGA

ACTTTAGCATCGCCTACAACATCGTGAAGATCCCCCCTCTGCAGGCTGACAAGGAGGATCCTATCTCTAAAAGTG

AAATTGTGGTCCAGTTCCCTTGTTCTGACCGGTTTAAGCCAAGTTACGTCCACTCATTCGGCCTGACACCAAACT

ATATCGTCTTTGTGGAGACTCCCGTGAAGATTAATCTGTTCAAATTTCTGAGCTCCTGGTCTCTGTGGGGGCTA

ACTACATGGACTGCTTCGAGAGTAATGAAACAATGGGAGTGTGGCTGCACATCGCAGATAAGAAACGAAAGAAAT

ACCTGAACAATAAGTACCGGACTAGCCCCTTCAACCTGTTTCACCATATCAACACCTATGAGGACAATGGATTTC

TGATTGTCGATCTGTGCTGTTGGAAGGGCTTCGAGTTCGTGTACAACTATCTGTACCTGGCAAACCTGCGCGAAA

ATTGGGAGGAAGTGAAGAAAAATGCTCGAAAAGCACCTCAGCCAGAAGTCAGGCGCTACGTGCTGCCACTGAACA

TCGACAAGGCTGATACAGGCAAAAACCTGGTGACTCTGCCCAATACCACAGCAACTGCCATCCTGTGCTCCGACG

AGACCATTTGGCTGGAGCCCGAAGTGCTGTTCTCTGGACCTCGCCAGGCCTTCGAATTTCCACAGATTAATTACC

AGAAGTACTGCGGCAAACCCTATACCTACGCTTATGGACTGGGCCTGAACCACTTCGTGCCTGATAGACTGTGCA

AGCTGAATGTCAAGACCAAAGAGACATGGGTGTGGCAGGAACCTGACTCATACCCCAGCGAGCCTATCTTTGTGA

GCCATCCAGATGCCCTGGAGGAAGACGATGGCGTGGTCCTGAGCGTGGTCGTGTCCCCAGGAGCAGGACAGAAGC

CAGCCTATCTGCTGATTCTGAACGCTAAAGATCTGTCCGAAGTGGCAAGAGCAGAGGTGGAGATCAATATCCCAG

TCACATTTCACGGGCTGTTCAAAAAGTCCTAA cDNA of human MERTK Genbank No. NM_006343.2

SEQ ID NO: 5

ATGGGGCCGGCCCCGCTGCCGCTGCTGCTGGGCCTCTTCCTCCCCGCGCTCTGGCGTAGAGCTATCACTGAGGCA

AGGGAAGAAGCCAAGCCTTACCCGCTATTCCCGGGACCTTTTCCAGGGAGCCTGCAAACTGACCACACACCGCTG

TTATCCCTTCCTCACGCCAGTGGGTACCAGCCTGCCTTGATGTTTTCACCAACCCAGCCTGGAAGACCACATACA

GGAAACGTAGCCATTCCCCAGGTGACCTCTGTCGAATCAAAGCCCCTACCGCCTCTTGCCTTCAAACACACAGTT

GGACACATAATACTTTCTGAACATAAAGGTGTCAAATTTAATTGCTCAATCAGTGTACCTAATATATACCAGGAC

ACCACAATTTCTTGGTGGAAAGATGGGAAGGAATTGCTTGGGGCACATCATGCAATTACACAG

TTTTATCCAGATGATGAAGTTACAGCAATAATCGCTTCCTTCAGCATAACCAGTGTGCAGCGTTCAGACAATGGG

TCGTATATCTGTAAGATGAAAATAAACAATGAAGAGATCGTGTCTGATCCCATCTACATCGAAGTACAAGGACTT

CCTCACTTTACTAAGCAGCCTGAGAGCATGAATGTCACCAGAAACACAGCCTTCAACCTCACCTGTCAGGCTGTG

GGCCCGCCTGAGCCCGTCAACATTTTCTGGGTTCAAAACAGTAGCCGTGTTAACGAACAGCCTGAAAAATCCCCC

```
TCCGTGCTAACTGTTCCAGGCCTGACGGAGATGGCGGTCTTCAGTTGTGAGGCCCACAATGACAAAGGGCTGACC

GTGTCCAAGGGAGTGCAGATCAACATCAAAGCAATTCCCTCCCCACCAACTGAAGTCAGCATCCGTAACAGCACT

GCACACAGCATTCTGATCTCCTGGGTTCCTGGTTTTGATGGATACTCCCCGTTCAGGAATTGCAGCATTCAGGTC

AAGGAAGCTGATCCGCTGAGTAATGGCTCAGTCATGATTTTTAACACCTCTGCCTTACCACATCTGTACCAAATC

AAGCAGCTGCAAGCCCTGGCTAATTACAGCATTGGTGTTTCCTGCATGAATGAAATAGGCTGGTCTGCAGTGAGC

CCTTGGATTCTAGCCAGCACGACTGAAGGAGCCCCATCAGTAGCACCTTTAAATGTCACTGTGTTTCTGAATGAA

TCTAGTGATAATGTGGACATCAGATGGATGAAGCCTCCGACTAAGCAGCAGGATGGAGAACTGGTGGGCTACCGG

ATATCCCACGTGTGGCAGAGTGCAGGGATTTCCAAAGAGCTCTTGGAGGAAGTTGGCCAGAATGGCAGCCGAGCT

CGGATCTCTGTTCAAGTCCACAATGCTACGTGCACAGTGAGGATTGCAGCCGTCACCAGAGGGGAGTTGGGCCC

TTCAGTGATCCAGTGAAAATATTTATCCCTGCACACGGTTGGGTAGATTATGCCCCCTCTTCAACTCCGGCGCCT

GGCAACGCAGATCCTGTGCTCATCATCTTTGGCTGCTTTTGTGGATTTATTTTGATTGGGTTGATTTTATACATC

TCCTTGGCCATCAGAAAAAGAGTCCAGGAGACAAAGTTTGGGAATGCATTCACAGAGGAGGATTCTGAATTAGTG

GTGAATTATATAGCAAAGAAATCCTTCTGTCGGCGAGCCATTGAACTTACCTTACATAGCTTGGGAGTCAGTGAG

GAACTACAAAATAAACTAGAAGATGTTGTGATTGACAGGAATCTTCTAATTCTTGGAAAAATTCTGGGTGAAGGA

GAGTTTGGGTCTGTAATGGAAGGAAATCTTAAGCAGGAAGATGGGACCTCTCTGAAAGTGGCAGTGAAGACCATG

AAGTTGGACAACTCTTCACAGCGGGAGATCGAGGAGTTTCTCAGTGAGGCAGCGTGCATGAAAGACTTCAGCCAC

CCAAATGTCATTCGACTTCTAGGTGTGTGTATAGAAATGAGCTCTCAAGGCATCCCAAAGCCCATGGTAATTTTA

CCCTTCATGAAATACGGGGACCTGCATACTTACTTACTTTATTCCCGATTGGAGACAGGACCAAAGCATATTCCT

CTGCAGACACTATTGAAGTTCATGGTGGATATTGCCCTGGGAATGGAGTATCTGAGCAACAGGAATTTTCTTCAT

CGAGATTTAGCTGCTCGAAACTGCATGTTGCGAGATGACATGACTGTCTGTGTTGCGGACTTCGGCCTCTCTAAG

AAGATTTACAGTGGCGATTATTACCGCCAAGGCCGCATTGCTAAGATGCCTGTTAAATGGATCGCCATAGAAAGT

CTTGCAGACCGAGTCTACACAAGTAAAAGTGATGTGTGGGCATTTGGCGTGACCATGTGGGAAATAGCTACGCGG

GGAATGACTCCCTATCCTGGGGTCCAGAACCATGAGATGTATGACTATCTTCTCCATGGCCACAGGTTGAAGCAG

CCCGAAGACTGCCTGGATGAACTGTATGAAATAATGTACTCTTGCTGGAGAACCGATCCCTTAGACCGCCCCACC

TTTTCAGTATTGAGGCTGCAGCTAGAAAAACTCTTAGAAAGTTTGCCTGACGTTCGGAACCAAGCAGACGTTATT

TACGTCAATACACAGTTGCTGGAGAGCTCTGAGGGCCTGGCCCAGGGCTCCACCCTTGCTCCACTGGACTTGAAC

ATCGACCCTGACTCTATAATTGCCTCCTGCACTCCCCGCGCTGCCATCAGTGTGGTCACAGCAGAAGTTCATGAC

AGCAAACCTCATGAAGGACGGTACATCCTGAATGGGGGCAGTGAGGAATGGAAGATCTGACTTCTGCCCCCTCT

GCTGCAGTCACAGCTGAAAAGAACAGTGTTTTACCGGGGGAGAGACTTGTTAGGAATGGGGTCTCCTGGTCCCAT

TCGAGCATGCTGCCCTTGGGAAGCTCATTGCCCGATGAACTTTTGTTTGCTGACGACTCCTCAGAAGGCTCAGAA

GTCCTGATGTGA
``` cDNA of human LRAT Genbank No. NM_004744.3

SEQ ID NO: 6

```
ATGAAGAACCCCATGCTGGAGGTGGTGTCTTTACTACTGGAGAAGCTGCTCCTCATCTCCAACTTCACGCTCTTT

AGTTCGGGCGCCGCGGGCGAAGACAAAGGGAGGAACAGTTTTTATGAAACCAGCTCTTTCCACCGAGGCGACGTG

CTGGAGGTGCCCCGGACCCACCTGACCCACTATGGCATCTACCTAGGAGACAACCGTGTTGCCCACATGATGCCC

GACATCCTGTTGGCCCTGACAGACGACATGGGCGCACGCAGAAGGTGGTCTCCAACAAGCGTCTCATCCTGGGC

GTTATTGTCAAAGTGGCCAGCATCCGCGTGGACACAGTGGAGGACTTCGCCTACGGAGCTAACATCCTGGTCAAT

CACCTGGACGAGTCCCTCCAGAAAAAGGCACTGCTCAACGAGGAGGTGGCGCGGAGGGCTGAAAAGCTGCTGGGC

TTTACCCCCTACAGCCTGCTGTGGAACAACTGCGAGCACTTCGTGACCTACTGCAGATATGGCACCCCGATCAGT
```

CCCCAGTCCGACAAGTTTTGTGAGACTGTGAAGATAATTATTCGTGATCAGAGAAGTGTTCTTGCTTCAGCAGTC

TTGGGATTGGCGTCTATAGTCTGTACGGGCTTGGTATCATACACTACCCTTCCTGCAATTTTTATTCCATTCTTC

CTATGGATGGCTGGCTAA cDNA of human TYR Genbank No. NM_000372.4

SEQ ID NO: 7

ATGCTCCTGGCTGTTTTGTACTGCCTGCTGTGGAGTTTCCAGACCTCCGCTGGCCATTTCCCTAGAGCCTGTGTC

TCCTCTAAGAACCTGATGGAGAAGGAATGCTGTCCACCGTGGAGCGGGGACAGGAGTCCCTGTGGCCAGCTTTCA

GGCAGAGGTTCCTGTCAGAATATCCTTCTGTCCAATGCACCACTTGGGCCTCAATTTCCCTTCACAGGGGTGGAT

GACCGGGAGTCGTGGCCTTCCGTCTTTTATAATAGGACCTGCCAGTGCTCTGGCAACTTCATGGGATTCAACTGT

GGAAACTGCAAGTTTGGCTTTTGGGGACCAAACTGCACAGAGAGACGACTCTTGGTGAGAAGAAACATCTTCGAT

TTGAGTGCCCCAGAGAAGGACAAATTTTTTGCCTACCTCACTTTAGCAAAGCATACCATCAGCTCAGACTATGTC

ATCCCCATAGGGACCTATGGCCAAATGAAAAATGGATCAACACCCATGTTTAACGACATCAATATTTATGACCTC

TTTGTCTGGATGCATTATTATGTGTCAATGGATGCACTGCTTGGGGATCTGAAATCTGGAGAGACATTGATTTT

GCCCATGAAGCACCAGCTTTTCTGCCTTGGCATAGACTCTTCTTGTTGCGGTGGGAACAAGAAATCCAGAAGCTG

ACAGGAGATGAAAACTTCACTATTCCATATTGGGACTGGCGGGATGCAGAAAAGTGTGACATTTGCACAGATGAG

TACATGGGAGGTCAGCACCCCACAAATCCTAACTTACTCAGCCCAGCATCATTCTTCTCCTCTTGGCAGATTGTC

TGTAGCCGATTGGAGGAGTACAACAGCCATCAGTCTTTATGCAATGGAACGCCCGAGGGACCTTTACGGCGTAAT

CCTGGAAACCATGACAAATCCAGAACCCCAAGGCTCCCCTCTTCAGCTGATGTAGAATTTTGCCTGAGTTTGACC

CAATATGAATCTGGTTCCATGGATAAAGCTGCCAATTTCAGCTTTAGAAATACACTGGAAGGATTTGCTAGTCCA

CTTACTGGGATAGCGGATGCCTCTCAAAGCAGCATGCACAATGCCTTGCACATCTATATGAATGGAACAATGTCC

CAGGTACAGGGATCTGCCAACGATCCTATCTTCCTTCTTCACCATGCATTTGTTGACAGTATTTTTGAGCAGTGG

CTCCGAAGGCACCGTCCTCTTCAAGAAGTTTATCCAGAAGCCAATGCACCCATTGGACATAACCGGGAATCCTAC

ATGGTTCCTTTTATACCACTGTACAGAAATGGTGATTTCTTTATTTCATCCAAAGATCTGGGCTATGACTATAGC

TATCTACAAGATTCAGACCCAGACTCTTTTCAAGACTACATTAAGTCCTATTTGGAACAAGCGAGTCGGATCTGG

TCATGGCTCCTTGGGGCGGCGATGGTAGGGGCCGTCCTCACTGCCCTGCTGGCAGGGCTTGTGAGCTTGCTGTGT

CGTCACAAGAGAAAGCAGCTTCCTGAAGAAAAGCAGCCACTCCTCATGGAGAAAGAGGATTACCACAGCTTGTAT

CAGAGCCATTTATAA cDNA of human GRP143 Genbank No. NM_000273.2

SEQ ID NO: 8

ATGACCCAGGCAGGCCGGCGGGGTCCTGGCACACCCGAGCCGCGTCCGCGAACACAGCCCATGGCCTCCCCGCGC

CTAGGGACCTTCTGCTGCCCCACGCGGGACGCAGCCACGCAGCTCGTGCTGAGCTTCCAGCCGCGGGCCTTCCAC

GCGCTCTGCCTGGGCAGCGGCGGGCTCCGCTTGGCGCTGGGCCTTCTGCAGCTGCTGCCCGGCCGCCGGCCCGCG

GGCCCCGGGTCCCCCGCGACGTCCCCGCCGGCCTCGGTCCGCATCCTGCGCGCTGCCGCTGCCTGCGACCTTCTC

GGCTGCCTGGGTATGGTGATCCGGTCCACCGTGTGGTTAGGATTCCCAAATTTTGTTGACAGCGTCTCGGATATG

AACCACACGGAAATTTGGCCTGCTGCTTTCTGCGTGGGGAGTGCGATGTGGATCCAGCTGTTGTACAGTGCCTGC

TTCTGGTGGCTGTTTTGCTATGCAGTGGATGCTTATCTGGTGATCCGGAGATCGGCAGGACTGAGCACCATCCTG

CTGTATCACATCATGGCGTGGGGCCTGGCCACCCTGCTCTGTGTGGAGGGAGCCGCCATGCTCTACTACCCTTCC

GTGTCCAGGTGTGAGCGGGCCTGGACCACGCCATCCCCACTATGTCACCATGTACCTGCCCCTGCTGCTGGTT

CTCGTGGCGAACCCCATCCTGTTCCAAAAGACAGTGACTGCAGTGGCCTCTTTACTTAAAGGAAGACAAGGCATT

TACACGGAGAACGAGAGGAGGATGGGAGCCGTGATCAAGATCCGATTTTTCAAAATCATGCTGGTTTTAATTATT

TGTTGGTTGTCGAATATCATCAATGAAAGCCTTTTATTCTATCTTGAGATGCAAACAGATATCAATGGAGGTTCT

TTGAAACCTGTCAGAACTGCAGCCAAGACCACATGGTTTATTATGGGAATCCTGAATCCAGCCCAGGGATTTCTC

TTGTCTTTGGCCTTCTACGGCTGGACAGGATGCAGCCTGGGTTTTCAGTCTCCCAGGAAGGAGATCCAGTGGGAA

TCACTGACCACCTCGGCTGCTGAGGGGGCTCACCCATCCCCACTGATGCCCCATGAAAACCCTGCTTCCGGGAAG

GTGTCTCAAGTGGGTGGGCAGACTTCTGACGAAGCCCTGAGCATGCTGTCTGAAGGTTCTGATGCCAGCACAATT

GAAATTCACACTGCAAGTGAATCCTGCAACAAAAATGAGGGTGACCCTGCTCTCCAACCCATGGAGACCTATGA

---

The invention claimed is:

1. An expression construct comprising a promoter and an operably linked polynucleotide sequence, wherein the promoter consists of:
   (a) a sequence of no more than 800 contiguous nucleotides from SEQ ID NO:1 comprising nucleotides 12-761 of SEQ ID NO:2, or
   (b) a sequence having at least 90% sequence identity to said sequence of (a); and
   wherein the operably linked polynucleotide sequence comprises the sequence of SEQ ID NO: 4.

2. The expression construct of claim 1, wherein the promoter:
   (a) comprises the sequence of SEQ ID NO: 2, or
   (b) consists of a sequence with at least 90% sequence identity to said sequence of SEQ ID NO: 2, wherein the sequence of the promoter is no longer than 800 nucleotides.

3. A vector comprising an expression construct according to claim 1.

4. The vector according to claim 3, wherein the vector is a viral vector.

5. The vector according to claim 4, wherein the vector is an adeno-associated virus (AAV) vector or comprises an AAV genome or a derivative thereof.

6. The vector according to claim 5, wherein said derivative is a chimeric, shuffled or capsid modified derivative.

7. The vector according to claim 5, wherein said AAV genome is from a naturally derived serotype or isolate or clade of AAV.

8. The vector according to claim 7, wherein said AAV genome is from AAV serotype 2 (AAV2), AAV serotype 4 (AAV4), AAV serotype 5 (AAV5) or AAV serotype 8 (AAV8) and/or wherein the capsid is derived from AAV5 or AAV8.

9. The vector according to claim 8, wherein the genome is derived from AAV2 and the capsid is derived from AAV5 or AAV8.

10. A host cell that contains a vector of claim 3.

11. The cell according to claim 10 that is a HEK293 or HEK293T cell.

12. A pharmaceutical composition comprising a vector of claim 3 and a pharmaceutically acceptable carrier.

13. The expression construct of claim 1, wherein the promoter consists of a sequence of no more than 800 contiguous nucleotides from SEQ ID NO:1 comprising nucleotides 12-761 of SEQ ID NO:2.

14. The expression construct of claim 2, wherein the promoter comprises the sequence of SEQ ID NO: 2.

15. A promoter which: (a) comprises the sequence of SEQ ID NO: 2, or (b) consists of a sequence having at least 90% sequence identity to said sequence of SEQ ID NO: 2, wherein the sequence of the promoter is no longer than 800 nucleotides.

16. A vector comprising a promoter according to claim 15.

17. The vector according to claim 16, wherein the vector which is a viral vector.

18. An expression construct comprising the promoter of claim 15, operably linked to a polynucleotide sequence.

19. The expression construct according to claim 18, wherein the operably linked polynucleotide sequence is an RPE65, MERTK, LRAT, TYR, GRP143 or MY07A coding sequence, or a sequence encoding a neurotrophic factor, an anti-angiogenic polypeptide or a polypeptide with anti-apoptotic effects in the RPE.

20. The expression construct according to claim 19, wherein the operably linked polynucleotide sequence comprises a sequence selected from SEQ ID NOs: 3 to 8, or that has at least 80% sequence identity to any one of SEQ ID NOs: 3 to 8.

21. A promoter consisting of:
   (a) a sequence of no more than 800 contiguous nucleotides from SEQ ID NO:1 comprising nucleotides 12-761 of SEQ ID NO:2, or
   (b) a sequence having at least 90% sequence identity to said sequence of (a).

* * * * *